US012427316B2

(12) United States Patent
Raike et al.

(10) Patent No.: US 12,427,316 B2
(45) Date of Patent: Sep. 30, 2025

(54) DIRECTIONAL SENSING FOR PROGRAMMING GUIDANCE

(71) Applicant: Medtronic, Inc., Minneapolis, MN (US)

(72) Inventors: Robert S. Raike, Minneapolis, MN (US); Jadin C. Jackson, Roseville, MN (US); Scott R. Stanslaski, Shoreview, MN (US); Eric J. Panken, Edina, MN (US); Christopher L. Pulliam, Plymouth, MN (US); Timothy R. Abraham, Lino Lakes, MN (US); Michelle A. Case, Blaine, MN (US); Paula Andrea Elma Dassbach Green, Minneapolis, MN (US); Abbey Beuning Holt Becker, Shoreview, MN (US); Rene A. Molina, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 236 days.

(21) Appl. No.: 17/462,676

(22) Filed: Aug. 31, 2021

(65) Prior Publication Data
US 2022/0062640 A1 Mar. 3, 2022

Related U.S. Application Data

(60) Provisional application No. 63/072,654, filed on Aug. 31, 2020.

(51) Int. Cl.
*A61N 1/36* (2006.01)
*A61N 1/05* (2006.01)

(52) U.S. Cl.
CPC ....... *A61N 1/36139* (2013.01); *A61N 1/0534* (2013.01); *A61N 1/36067* (2013.01)

(58) Field of Classification Search
CPC .............. A61N 1/36139; A61N 1/0534; A61N 1/36067; A61N 1/0529; A61N 1/0531;
(Continued)

(56) References Cited

U.S. PATENT DOCUMENTS 8,849,392 B2   9/2014   Lozano
8,868,173 B2   10/2014  Nelson et al.
(Continued)

FOREIGN PATENT DOCUMENTS

WO    2003043690 A1   5/2003
WO    2017158067 A1   9/2017
WO    2017203301 A1   11/2017

OTHER PUBLICATIONS

U.S. Appl. No. 17/410,268, filed Aug. 24, 2021, naming inventors Jackson et al.
(Continued)

*Primary Examiner* — Benjamin J Klein
*Assistant Examiner* — Daniel Tehrani
(74) *Attorney, Agent, or Firm* — Shumaker & Sieffert, P.A.

(57) ABSTRACT

Devices, systems, and techniques for identifying electrodes closest to a target region of tissue are described. In one example, a device includes sensing circuitry configured to sense electrical signals from a plurality of electrode combinations. Processing circuitry identifies a first electrode combination of a first subset of electrode combinations. Each electrode combination of the first subset of electrode combination includes electrodes located at different axial positions along a length of the medical lead. The processing circuitry identifies a second electrode combination of a second subset of electrode combinations. Each electrode combination of the second subset of electrode combinations includes electrodes located at a same axial position and
(Continued)

different circumferential positions around a perimeter of the medical lead. The processing circuitry then determines a third electrode combination and controls delivery of electrical stimulation via the third electrode combination.

24 Claims, 16 Drawing Sheets

(58) Field of Classification Search
CPC .............. A61N 1/36185; A61N 1/3605; A61N 1/36082; A61N 1/36135; A61N 1/3614; A61N 1/36182; A61N 2001/083; A61N 1/36125; A61N 1/372; A61B 5/24; A61B 5/375; A61B 5/065; A61B 5/4076; A61B 5/6868; A61B 5/4836
See application file for complete search history.

(56) References Cited

U.S. PATENT DOCUMENTS

| | | | |
|---|---|---|---|
| 9,498,628 | B2 | 11/2016 | Kaemmerer et al. |
| 9,814,885 | B2 | 11/2017 | Molnar et al. |
| 10,857,364 | B1 * | 12/2020 | Soin .................. A61B 5/01 |
| 11,045,652 | B2 | 6/2021 | Jackson et al. |
| 11,135,429 | B2 | 10/2021 | Panken et al. |
| 11,318,296 | B2 | 5/2022 | Xiao et al. |
| 2011/0144715 | A1 | 6/2011 | Molnar et al. |
| 2014/0213926 | A1 * | 7/2014 | Vaidyanathan ........ A61B 5/375 600/545 |
| 2016/0120432 | A1 | 5/2016 | Sridhar et al. |
| 2017/0259064 | A1 * | 9/2017 | Wu .................... A61N 1/36067 |
| 2018/0280699 | A1 | 10/2018 | Arlotti et al. |
| 2019/0030321 | A1 | 1/2019 | Tinkhauser et al. |
| 2019/0126029 | A1 | 5/2019 | Cheeran et al. |
| 2019/0143120 | A1 | 5/2019 | Sinclair et al. |
| 2020/0129757 | A1 | 4/2020 | Xiao et al. |
| 2020/0338351 | A1 | 10/2020 | Panken et al. |
| 2022/0009684 | A1 | 1/2022 | Naderi |
| 2022/0032059 | A1 | 2/2022 | Molina et al. |
| 2022/0032063 | A1 | 2/2022 | Molina et al. |
| 2022/0126100 | A1 | 4/2022 | Jackson et al. |

OTHER PUBLICATIONS

U.S. Appl. No. 17/651,500, filed Feb. 17, 2022, naming inventors Jackson et al.

Ince et al., "Selection of Optimal Programming Contacts Based on Local Field Potential Recordings Form Subthalamic Nucleus in Patients with Parkinson's Disease," NIH Public Access, Neurosurgery, vol. 67, No. 2, doi:10.1227/01.NEU.0000372091.64824.63, Aug. 2010, pp. 390-397.

International Search Report and Written Opinion of International Application No. PCT/US2021/048449, dated Jan. 14, 2022, 11 pp.

Tinkhauser et al., "Directional Local Field Potentials: A Tool to Optimize Deep Brain Stimulation," Wiley Online, Movement Disorders, vol. 00, No. 00, DOI: 10.1002/mds.27215, Oct. 3, 2017, 6 pp.

U.S. Appl. No. 17/650,038, filed Feb. 4, 2022, naming inventors Case et al.

Office Action from U.S. Appl. No. 17/650,038 dated Jul. 1, 2024, 21 pp.

Response to Office Action dated Jul. 1, 2024 from U.S. Appl. No. 17/650,038, filed Oct. 1, 2024, 14 pp.

Advisory Action from U.S. Appl. No. 17/650,038 dated Mar. 12, 2025, 5 pp.

Response to Final Office Action dated Dec. 16, 2024 from U.S. Appl. No. 17/650,038, filed Feb. 17, 2025, 12 pp.

Final Office Action from U.S. Appl. No. 17/650,038 dated Dec. 16, 2024, 18 pp.

* cited by examiner

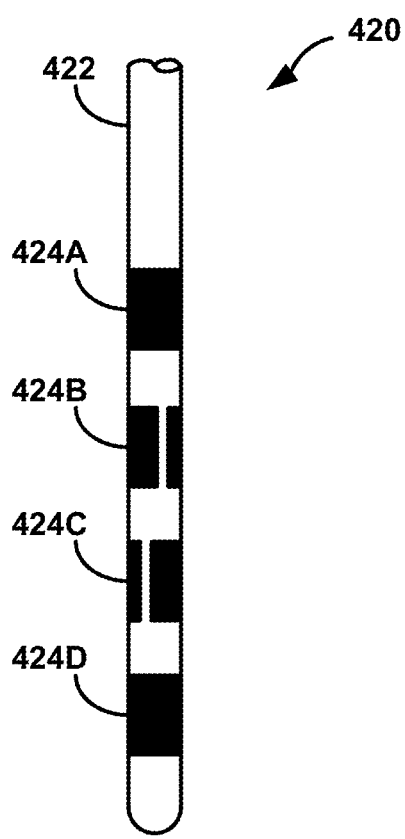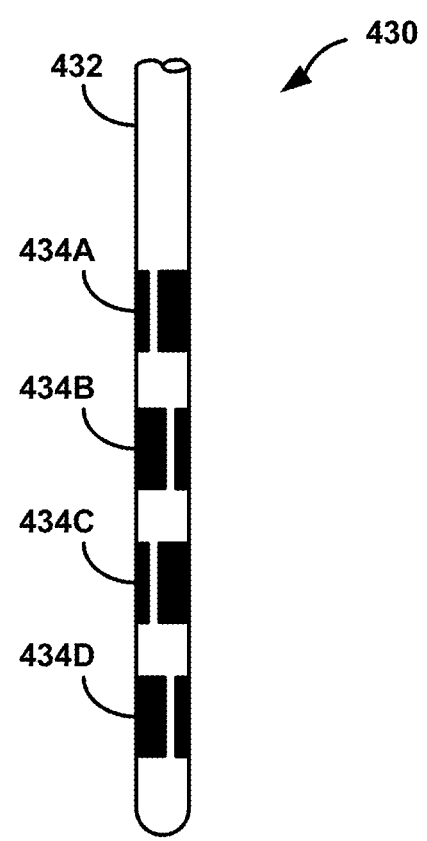
FIG. 4C                    FIG. 4D

FIG. 10A
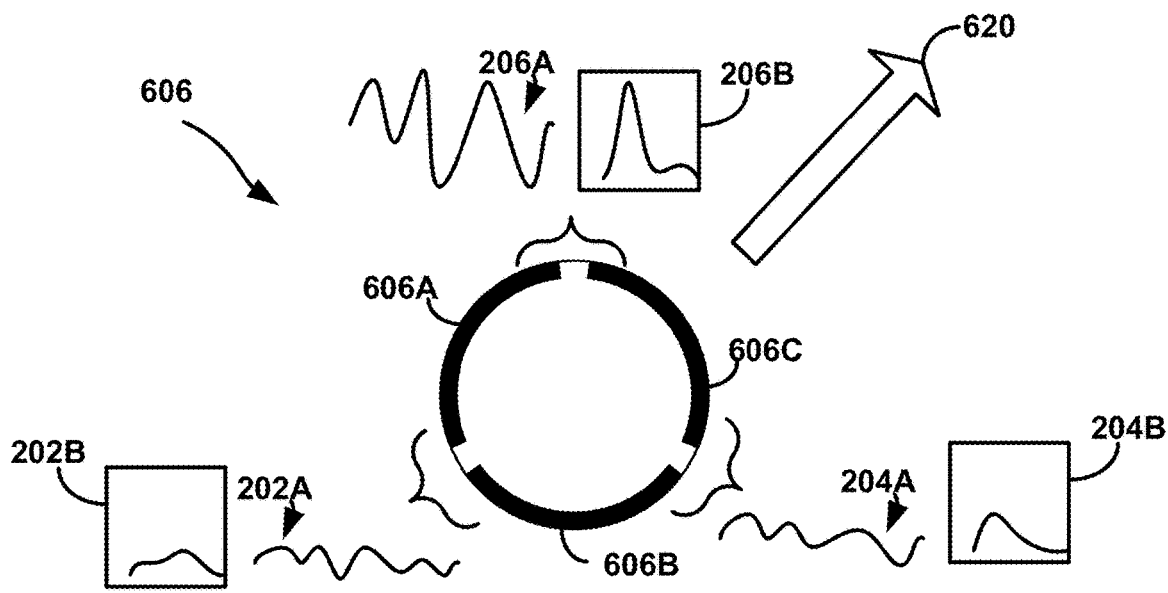
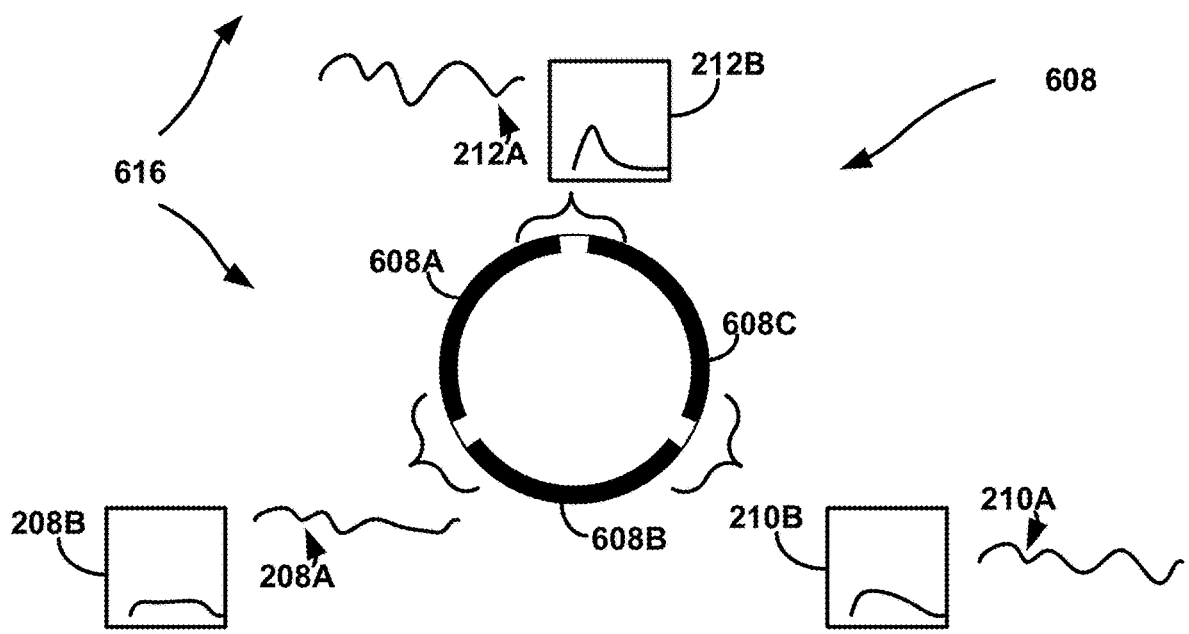
FIG. 10B

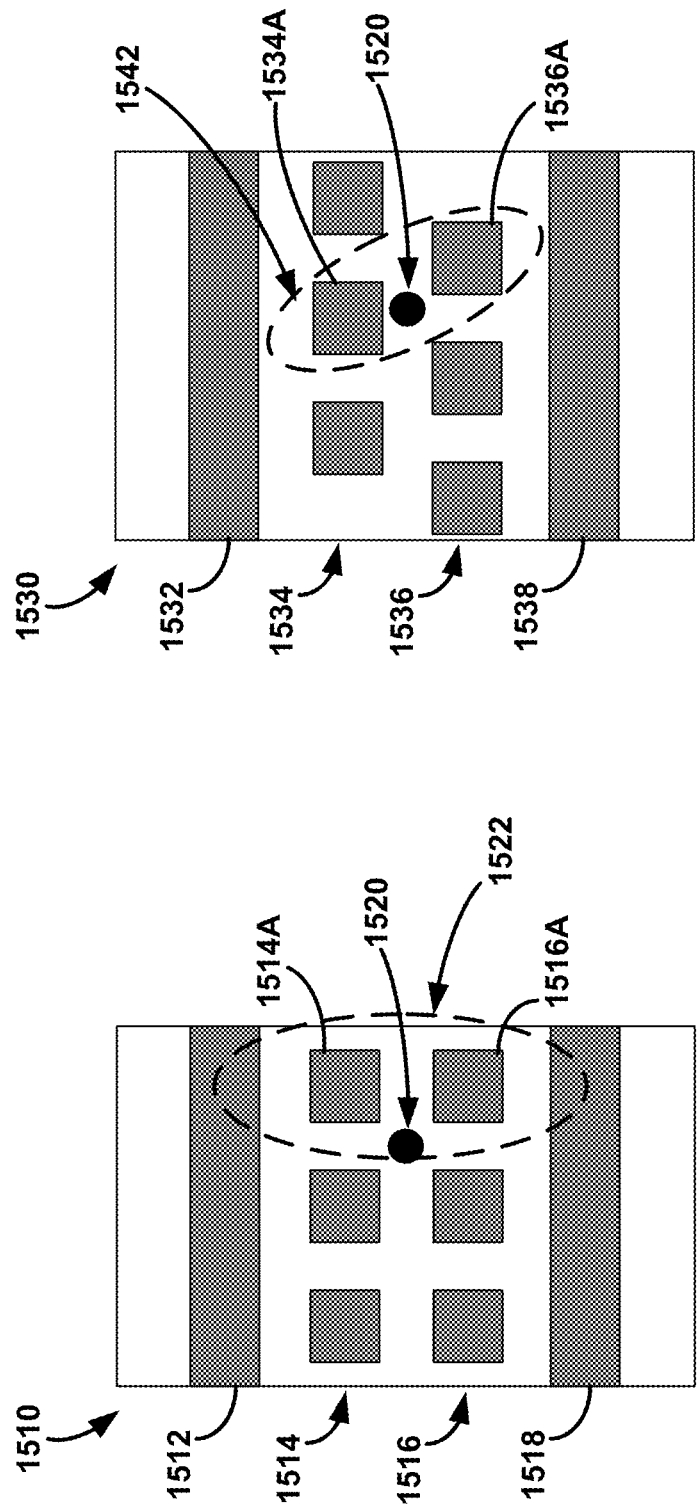

DIRECTIONAL SENSING FOR PROGRAMMING GUIDANCE

This application claims the benefit of U.S. Provisional Patent Application No. 63/072,654, filed Aug. 31, 2020, the entire content of which is incorporated herein by reference.

TECHNICAL FIELD

The disclosure relates to medical devices, and more specifically, sensing electrical signals from a patient.

BACKGROUND

Implantable medical devices, such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agents, insulin, pain relieving agents or anti-inflammatory agents to a target tissue site within a patient. In some therapy systems, an implantable electrical stimulator delivers electrical therapy to a target tissue site within a patient with the aid of one or more electrodes, that may be deployed by medical leads and/or on a housing of the electrical stimulator, or both. In some therapy systems, therapy may be delivered via particular combinations of the electrodes carried by leads and/or by the housing of the electrical stimulator.

During a programming session, that may occur during implant of the medical device, during a trial session, or during an in-clinic or remote follow-up session after the medical device is implanted in the patient, a clinician may generate one or more therapy programs (also referred to as therapy parameter sets) that are found to provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. In examples in that electrical stimulation is delivered in the form of electrical pulses, for example, the therapy parameters may include an electrode configuration including an electrode combination and electrode polarities, an amplitude, that may be a current or voltage amplitude, a pulse width, and a pulse rate.

SUMMARY

In general, the disclosure is directed to devices, systems, and methods for utilizing brain signals, such as LFPs (local field potential), to identify electrodes on an implantable lead that are closest to a target region of tissue (e.g., of the STN (subthalamic nucleus)). Such a region may generate signals of interest (e.g., beta waves that are indicative of areas of the brain causing Parkinson's tremors). In this manner, the system may sense signals between different combinations of electrodes in order to highlight relevant differences between each of the electrodes. The system may then generate information regarding these signals and inform the implanting physician of these signals. The sensed signals may be between electrodes at different circumferential positions or electrodes at different axial positions (e.g., bipolar sensing). The physician, or the system, may then determine parameters for directional stimulation using these obtained directional signals (e.g., the LFP distribution) instead of having to test stimulation provided by each electrode combination.

As one example, a method includes sensing, by sensing circuitry, electrical signals from a plurality of electrode combinations. Each electrode of the plurality of electrode combinations is carried by a medical lead. The medical lead includes electrodes at different axial positions along a length of the medical lead and at different circumferential positions around a perimeter of the medical lead. The method includes identifying, by processing circuitry and based on sensed electrical signals from a first subset of electrode combinations of the plurality of electrode combinations, a first electrode combination of the first subset of electrode combinations. Each electrode combination of the first subset of electrode combination includes electrodes located at different axial positions along the length of the medical lead. The method includes identifying, by the processing circuitry and based on sensed electrical signals from a second subset of electrode combinations of the plurality of electrode combinations, a second electrode combination of the second subset of electrode combinations. Each electrode combination of the second subset of electrode combinations includes electrodes located at a same axial position and different circumferential positions around the perimeter of the medical lead. The method includes determining, by the processing circuitry and based on the first electrode combination and the second electrode combination, a third electrode combination and controlling, by the processing circuitry, delivery of electrical stimulation via the third electrode combination.

As another example, a device includes sensing circuitry configured to sense electrical signals from a plurality of electrode combinations. Each electrode of the plurality of electrode combinations is carried by a medical lead. The medical lead includes electrodes at different axial positions along a length of the medical lead and at different circumferential positions around a perimeter of the medical lead. The device includes processing circuitry configured to identify, based on sensed electrical signals from a first subset of electrode combinations of the plurality of electrode combinations, a first electrode combination of the first subset of electrode combinations. Each electrode combination of the first subset of electrode combination includes electrodes located at different axial positions along the length of the medical lead. The processing circuitry is configured to identify, based on sensed electrical signals from a second subset of electrode combinations of the plurality of electrode combinations, a second electrode combination of the second subset of electrode combinations. Each electrode combination of the second subset of electrode combinations includes electrodes located at a same axial position and different circumferential positions around the perimeter of the medical lead. The processing circuitry is also configured to determine, based on the first electrode combination and the second electrode combination, a third electrode combination and control delivery of electrical stimulation via the third electrode combination.

As another example, a computer-readable storage medium includes instructions that, when executed, cause processing circuitry to receive signal information indicative of first electrical signals sensed from a plurality of electrode combinations. Each electrode of the plurality of electrode combinations is carried by a medical lead. The medical lead includes electrodes at different axial positions along a length of the medical lead and at different circumferential positions around a perimeter of the medical lead. The instructions identifying a first electrode combination of a first subset of electrode combinations of the plurality of electrode combinations based on signal information from the first subset of electrode combinations of the plurality of electrode combinations. Each electrode combination of the first subset of electrode combination includes electrodes located at different axial positions along the length of the medical lead. The instructions identifying a second electrode combination of a second subset of electrode combinations of the plurality of electrode combinations based on signal information from a second subset of electrode combinations of the plurality of electrode combinations. Each electrode combination of the second subset of electrode combinations includes electrodes located at a same axial position and different circumferential positions around the perimeter of the medical lead. The instructions determining a third electrode combination based on the first electrode combination and the second electrode combination; and controlling delivery of electrical stimulation via the third electrode combination.

The details of one or more examples are set forth in the accompanying drawings and the description below. Other features, objects, and advantages will be apparent from the description and drawings, and from the claims.

BRIEF DESCRIPTION OF DRAWINGS

FIGS. 4A, 4B, 4C, and 4D are conceptual diagrams of example leads with respective electrodes carried by the lead.

FIGS. 10A and 10B are a conceptual diagram of example waveform amplitudes sensed by electrode combinations located at different circumferential positions of a medical lead in accordance with one or more techniques of this disclosure.

FIG. 15A is a conceptual diagram of an example lead with aligned circumferential electrodes and resulting sensing field.

FIG. 15B is a conceptual diagram of an example lead with offset circumferential electrodes and resulting sensing field.

DETAILED DESCRIPTION

Figure 1:
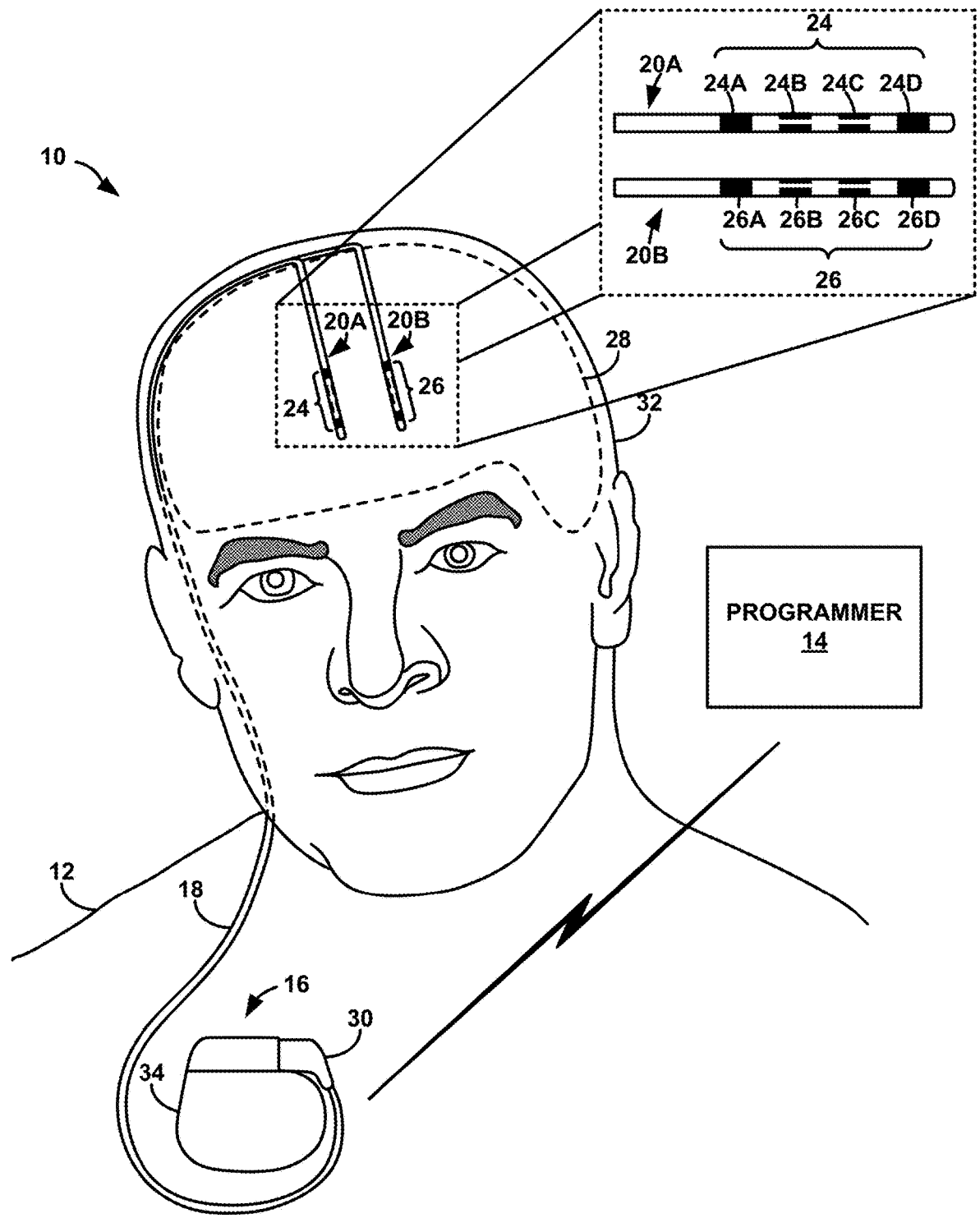
FIG. 1 is a conceptual diagram illustrating an example deep brain stimulation (DBS) system configured to deliver electrical stimulation therapy to a tissue site within a brain of a patient.

In general, the disclosure is directed to utilizing sensed electrical signals, such as LFPs within the brain, to identify electrodes on an implantable lead that are closest to a target region of tissue (e.g., the STN) and may be appropriate to deliver electrical stimulation. Many brain disorders may be associated with abnormal brain function. In one example, Parkinson's Disease (PD) is a progressive neuro-degenerative disorder characterized by the depletion of dopaminergic neurons in the basal ganglia-thalamo-cortical network. As PD progresses, the manifestations of the disease may include one or more of the characteristic motor dysfunctions that include one or more of akinesia, bradykinesia, rigidity, and tremor. In some examples, deep brain stimulation (DBS) therapy may be used to deliver electrical stimulation to treat motor symptoms in medication-refractory PD patients. In some examples, DBS therapy may involve the unilateral or bilateral implantation of one or more leads into the brain to deliver electrical stimulation to target structures in the basal ganglia. Selection of effective stimulation parameters for DBS therapy may be time-consuming for both the clinician (e.g., a physician, nurse, or technician) and the patient. As such, it may be desirable to reduce the amount of time consumed to select stimulation parameters. In addition, the trial-and-error approach for determining appropriate electrode combinations and/or other stimulation parameters may subject the patient to undesirable side effects during this process.

The target region associated with a disease (e.g., PD) may generate signals of interest (e.g., Beta waves that may be indicative of symptoms such as tremor in PD). As described herein, a system may sense signals between different combinations of electrodes in order to highlight relevant differences between the sensed signals from each of the electrodes. The system may then generate information regarding these signals, such as information that may be presented to a clinician and/or information used by the system to select parameter values for stimulation such as an electrode combination. The sensed signals may be between electrodes at different circumferential positions or electrodes at different axial positions on the same medical lead (e.g., bipolar sensing). Monopolar sensing may be utilized in other examples, wherein monopolar sensing includes sensing between a lead electrode and a remote electrode (e.g., an electrode or electrodes located on a different lead or housing of the IMD at a sufficient distance from the desired sensing location). Monopolar sensing may be utilized for sensing between electrodes of a lead that only has a single axial level of electrodes at different circumferential positions, in one example. The physician, or the system, may then determine parameters for directional stimulation based on one or more characteristics of these obtained signals (e.g., a directional LFP distribution) instead of having to test stimulation provided by each electrode combination.

For example, a Beta rhythm may be localized with the dorsal STN. It may be helpful to select stimulation electrodes that may generate an electric field that affects this oscillatory region of the brain. The system may detect electrical signals between different electrode combinations and process the signals to generate spectral power characteristics for one or more frequencies. The system may then identify the electrode combinations, and thus axial (or level) and circumferential positions of the electrode combinations, associated with the spectral power characteristics indicative of stronger Beta waves. For example, higher amplitudes of the spectral power for frequencies indicative of Beta waves indicate that those electrode combinations are closer to the originating source of the Beta waves. In some examples, the system may select these closer electrode combinations for targeted stimulation to this region of tissue. In addition, or alternatively, the system may present this information to a clinician to enable the clinician to review the LFPs sensed (and/or characteristics such as spectral power) from different electrode combinations. The clinician may then select an electrode combination associated with the stronger (e.g., larger amplitude spectral power) electrode amplitudes associated with Beta waves for subsequent sensing and/or stimulation therapy.

The medical lead may have electrodes disposed at different axial positions along the length of the lead. These electrodes may be ring electrodes and/or electrodes that only reside around a limited portion of the perimeter of the lead. In this manner, the medical lead may have electrodes at different circumferential positions (e.g., at different positions around the perimeter of the lead) and at the same axial position along the length of the lead (e.g., on the same level of the lead). In some examples, the system may group electrodes together as one polarity for use with another electrode of another polarity. The system may perform such groupings in order to balance impedance between cathodes and anodes and improve sensing fidelity. In one example, to sense between a level with a ring electrode and a level with multiple smaller electrodes at different circumferential positions, the system may gang together those electrodes at different circumferential positions to create a virtual ring electrode that may improve sensing between an actual ring electrode.

Sensing electrical signals between different electrodes, electrodes at different axial positions and at different circumferential positions, may provide valuable information about where certain electrical signals (e.g., signals in the Beta frequency band or Beta waves, alpha waves, gamma waves, theta waves, and high frequency oscillations (HFO)) are originating from within tissue. In this manner, the system (or a physician) may use this information to identify where a target region of tissue (e.g., the STN) is located and determine that electrodes (and/or other stimulation parameter values) should be used to deliver electrical stimulation therapy. In one example, the system may provide information representative of the sensed electrical signals via a display to enable a clinician to program stimulation more effectively and in less time than using other trial-and-error approaches.

FIG. 1 is a conceptual diagram illustrating an example therapy system 10 that is configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. 1 MB 16 includes a stimulation generator (not shown in FIG. 1) configured to generate and deliver electrical stimulation therapy to the STN region of brain 28 of patient 12 via one or more electrodes 24, 26 of leads 20A and 20B, respectively.

In the example shown in FIG. 1, therapy system 10 may be referred to as a deep brain stimulation (DBS) system because 1 MB 16 is configured to deliver electrical stimulation therapy directly to the STN within brain 28. DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post-traumatic stress disorder, dysthymic disorder, and obsessive compulsive disorder (OCD)), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12. Although system 10 is generally described as being used to deliver DBS or sense signals related to the treatment of symptoms related to brain 28, system 10 may be used to sense signals or deliver therapy to other anatomical locations, such as the spinal cord, peripheral nerves, pelvic floor nerves, or any other anatomical structure or treat symptoms associated with other anatomical structures.

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), that may include, for example, electrical electrodes that electrically couple to respective electrodes on lead extension 18. The electrical electrodes electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 may be constructed of a biocompatible material that resists corrosion and degradation from bodily fluids. IMD 16 may comprise a hermetically sealed housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, that may be selected based on many factors, such as the type of patient condition therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 such that electrodes 24, 26 are capable of providing electrical stimulation to target therapy delivery sites within brain 28 during treatment. In the case of Parkinson's disease, for example, leads 20 may be implanted to deliver electrical stimulation to regions within the STN, either unilaterally or bilaterally. Target therapy delivery sites not located in brain 28 of patient 12 are also contemplated.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In the examples shown in FIG. 1, electrodes 24, 26 of leads 20 are shown as ring electrodes. Ring electrodes may be relatively easy to program and may be capable of delivering an electrical field to any tissue adjacent to leads 20. In other examples, electrodes 24, 26 of leads 20 may have different configurations. For example, one or more of the electrodes 24, 26 of leads 20 may have a complex electrode array geometry that is capable of producing shaped electrical fields, including interleaved stimulation. An example of a complex electrode array geometry may include an array of electrodes positioned at different axial positions along the length of a lead, as well as at different angular (or circumferential) positions about the periphery, e.g., circumference, of the lead. The complex electrode array geometry may include multiple electrodes (e.g., partial ring or segmented electrodes), such as electrode levels 24B, 24C, 26B, and 26C that each include multiple individually programmable electrodes located at different positions around the perimeter of each respective lead 20. Although electrodes 24A, 24D, 26A, and 26D may be ring electrodes that each extend fully around the perimeter of the lead, any of these electrodes may be replaced by multiple electrodes located at different positions around the perimeter of the lead. By using electrodes disposed at different positions around the perimeter of the lead, electrical stimulation may be directed to a specific direction from leads 20 to enhance therapy efficacy and reduce possible adverse side effects from stimulating a large volume of tissue. As a further example, the electrodes may be pad electrodes, that may be carried on a paddle lead or a cylindrical lead.

As illustrated in the example of FIG. 1, the set of electrodes 24 of lead 20A may include electrodes 24A, 24B, 24C, and 24D, and the set of electrodes 26 of lead 20B may include electrodes 26A, 26B, 26C, and 26D. In some examples, each of electrodes 24 and 26 may be configured to independently deliver electrical stimulation.

In some examples, outer housing 34 of IMD 16 may include one or more stimulation and/or sensing electrodes. For example, housing 34 may comprise an electrically conductive material that is exposed to tissue of patient 12 when IMD 16 is implanted in patient 12, or an electrode may be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs (also referred to herein as "set of stimulation parameter values"). A stimulation therapy program may define one or more electrical stimulation parameter values for therapy generated by a stimulation generator (not shown in FIG. 1) of IMD 16 and delivered from IMD 16 to a target therapy delivery site within patient 12 via one or more electrodes 24, 26. The electrical stimulation parameters may define an aspect of the electrical stimulation therapy, and may include, for example, voltage or current amplitude of an electrical stimulation signal, a charge level of an electrical stimulation, a frequency of the electrical stimulation signal, waveform shape, on/off cycling state (e.g., if cycling is "off," stimulation is always on, and if cycling is "on," stimulation is cycled on and off) and, in the case of electrical stimulation pulses, pulse rate, pulse width, and other appropriate parameters such as duration or duty cycle. In addition, if different electrodes are available for delivery of stimulation, an electrode combination may further characterize a therapy parameter of a therapy program, that may define selected electrodes 24, 26 and their respective polarities. In some examples, stimulation may be delivered using a continuous waveform and the stimulation parameters may define this waveform.

In addition to being configured to deliver therapy to manage a disorder of patient 12, therapy system 10 may be configured to sense bioelectrical brain signals or another physiological parameter of patient 12. For example, IMD 16 may include a sensing circuitry that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the stimulation generator to target sites within brain 28 as well as sense brain signals within brain 28. However, IMD 16 may also use a separate set of sensing electrodes to sense the bioelectrical brain signals. In some examples, the sensing circuitry of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

External medical device programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device, voice activation, or another input mechanism that allows the user to navigate through the user interface of programmer 14 and provide input. If programmer 14 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, programmer 14 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit programming information to IMD 16. Programming information may include, for example, hardware information, such as the type of leads 20, the arrangement of electrodes 24, 26 on leads 20, the position of leads 20 within brain 28, one or more therapy programs defining therapy parameter values, therapeutic windows for one or more electrodes 24, 26, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. Programmer 14 may assist the clinician in the creation/identification of therapy programs by providing a system for identifying potentially beneficial therapy parameter values. For example, during a programming session, the physician may select an electrode combination for delivery of therapy to the patient. The physician may have the option to create several therapy programs. Some programs may have the same electrode combination (but different values of at least one other therapy parameter) and these therapy programs may be organized into subsets, each subset having the same electrode combination. The physician may select an efficacious therapy program for each subset based on a displayed list of sensed LFP signals from electrode combinations. The clinician may select a therapy program based on a list displayed on external programmer 14 of combinations of electrodes providing the largest LFP spectral power to provide therapy to patient 12 to address symptoms associated with the patient condition.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate with IMD 16 and, optionally, another computing device, via wireless communication. Programmer 14, for example, may communicate via wireless communication with IMD 16 using radio frequency (RF) and/or inductive telemetry techniques that may comprise techniques for proximal, mid-range, or longer-range communication. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards, or memory sticks. Further, programmer 14 may communicate with IMD 16 and another programmer via remote telemetry techniques known in the art, communicating via a personal area network (PAN), a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment. In another example, a clinician in an operating room may obtain acute recordings during lead placement and before coupling the lead with an IMD. In this example, an external device (e.g., an external electrophysiology system) may couple to the medical lead in order to obtain sensed electrical signals.

While DBS may successfully reduce symptoms of some neurological diseases, the stimulation may also cause unwanted side effects, also referred to herein as adverse effects. Side effects may include incontinence, tingling, loss of balance, paralysis, slurred speech, loss of memory, loss of inhibition, and many other neurological problems. Side effects may be mild to severe. DBS may cause one or more adverse effects by inadvertently providing electrical stimulation pulses to anatomical regions near the targeted anatomical region. These anatomical regions may be referred to as regions associated with adverse stimulation effects. For this reason, a clinician may program IMD 16 with a therapy program (or a plurality of therapy programs) that defines stimulation parameter values that balance effective therapy and minimize side effects.

With the aid of programmer 14 or another computing device, a clinician may select values for therapy parameters for therapy system 10, including an electrode combination. By selecting particular electrodes 24, 26 and electrode combinations for delivering electrical stimulation therapy to patient 12, a clinician may modify the electrical stimulation therapy to target one or more particular regions of tissue (e.g., specific anatomical structures) within brain 28 and avoid other regions of tissue within brain 28. In addition, by selecting values for the other stimulation parameter values that define the electrical stimulation signal, e.g., the amplitude, pulse width, and pulse rate, the clinician may generate an efficacious therapy for patient 12 that is delivered via the selected electrode subset. Due to physiological diversity, condition differences, and inaccuracies in lead placement, the parameter values may vary between patients.

During a programming session, the clinician may determine one or more therapy programs that may provide effective therapy to patient 12. Patient 12 may provide feedback to the clinician as to the efficacy of the specific program being evaluated, that may include information regarding adverse effects of delivery of therapy according to the specific program. In some examples, the patient feedback may be used to determine a clinical rating scale score. Once the clinician has identified one or more programs that may be beneficial to patient 12, patient 12 may continue the evaluation process and determine which program best alleviates the condition of patient 12 or otherwise provides efficacious therapy to patient 12. Programmer 14 may assist the clinician in the creation/identification of therapy programs by providing a methodical system of identifying potentially beneficial therapy parameters.

In accordance with one or more techniques of this disclosure, and as discussed in further detail below, in some examples, medical leads 20 may be offset, or set a distance, from a signal source (e.g., Beta waves may be largely localized within the dorsal STN) in patient tissue (e.g., where the signal source could be within the STN of the left and/or right hemisphere). If a medical lead 20 is placed within or having a common axis with a signal source, the system may not distinguish the direction a signal is coming from. For example, the signals sensed by respective electrodes of medical leads 20 may be similar to each other because of the proximity of the signal source. For example, if a medical lead 20 is disposed at the origin of a signal source, any signal emanating from the signal source may appear to be around the medical lead as opposed to appearing to be located at only one circumferential direction to the medical lead. In this situation, any of the electrode combinations may be selected for delivery of stimulation. However, a clinician may implant a medical lead to be offset from a target tissue location in order to target that target tissue location and prevent damage to that target tissue location that could occur by implantation of the lead. Information representative of signal magnitude over frequency (e.g., spectral density) between an electrode combination (e.g., bipolar review) may be displayed for a clinician who may be determining stimulation therapy for the patient. Bipolar sensing generally describes sensing between electrodes on the same lead. Monopolar sensing generally describes sensing between an electrode on a lead and a remote electrode (e.g., an electrode or electrodes located on a different lead or housing of the IMD at a sufficient distance from the desired sensing location). In this manner, monopolar sensing generally records electrical signals more prevalent around a desired electrode, whereas bipolar sensing senses electrical activity between two relatively close electrodes.

In another example, medical lead 20 may be implanted directly at the target tissue (e.g., in a region with the strongest beta oscillation or largest amplitude of a target frequency). In another example, medical lead 20 may be implanted based purely on anatomy alone (e.g., placed in the STN). In either of these examples, due to various uncertainties associated with the lead placement procedure, the location of the medical lead may not be the same as the region generating the maximal signal source, resulting in an offset between the target anatomy and the lead location. However, it is not necessary for medical lead 20 to be offset from the target anatomy as a lead placed at the target tissue that generates the strongest signal may provide effective stimulation therapy. A clinician may choose to implant medical lead 20 offset from target tissue or directly at or within the target tissue that generates the strongest signal.

When using medical leads with larger number of electrodes, the time necessary for a review by a clinician grows. Further, the exploration and programming time required for directional stimulation across multiple combinations of electrodes increases as well. To reduce the time required of the patient and the clinician, in some examples, a representation of signal strength sensed by multiple combinations of electrodes may be displayed to the clinician. The clinician may then select, or the system may automatically select, the electrode combination having the greatest signal strength (e.g., showing the largest Beta wave signal strength, gamma wave signal strength, alpha wave signal strength, or any frequency of a desired signal).

In some examples, a device (e.g., IMD 16) includes processing circuitry configured to identify a first electrode combination from a first subset of electrode combinations based on sensed electrical signals from the first subset of electrode combinations. Each electrode combination of the first subset of electrode combination may comprise electrodes located at different axial positions along the length of medical lead 20. The first electrode combination may provide insight for the clinician as to the electrode combination at an axial position that may provide efficacious stimulation therapy. That is, the first electrode combination providing the strongest sensed signal strength may indicate that the first electrode combination is closest to an axial location along lead 20 for which target tissue is located.

In some examples, the processing circuitry may identify a second electrode combination from a second subset of electrode combinations based on sensed electrical signals from the second subset of electrode combinations. Each electrode combination of the second subset of electrode combinations may comprise electrodes located at a same axial position and different circumferential positions around the perimeter of medical lead 20. The second electrode combination may provide insight for the clinician as to the electrode pair that provides directional stimulation therapy. That is, the second electrode combination providing the strongest sensed signal strength may indicate that the second electrode combination is closest to a circumferential position of medical lead 20 at which target tissue is located.

In some examples, the processing circuitry may determine a third electrode combination, based on the first electrode combination and the second electrode combination and then control delivery of electrical stimulation via the third electrode combination. In one example, the third electrode combination may be the same as the first electrode combination. In another example, the third electrode combination may be the same as the second electrode combination. In another example, the third electrode combination may be a combination of one electrode from the first electrode combination and one electrode from the second electrode combination. In yet another example, the third electrode combination may be an electrode combination located adjacent to or near the first electrode combination and the second electrode combination. In another example, the clinician may select, or the combination may be selected automatically by IMD 16 or programmer 14, based upon the axial height of the first electrode combination and the circumferential position of the second electrode combination. In any case, the third electrode combination may be selected according to the axial and circumferential location information obtained by identifying the first and second electrode combinations as discussed above.

In some examples, a device (e.g., IMD 16, programmer 14, and/or another computing device) may be configured to automatically sense electrical signals from an electrode combination of a plurality of combinations of electrodes. For instance, IMD 16 may sense electrical signals measured across one or more combinations of electrodes of a plurality of combinations of electrodes. As one example, IMD 16 may sense electrical signals (e.g., sub-microvolt LFPs) from combinations of electrodes 24 and/or electrodes 26.

These sensed electrical signals for the particular patient from combinations of electrodes 24 and/or electrodes 26 may be represented on a display or user interface (not shown in FIG. 1) at programmer 14, and/or another computing device. A clinician may select an electrode combination to provide stimulation therapy based on sensed signals from a plurality of electrode combinations. For instance, a clinician may select an electrode combination using one or more of electrodes 24, electrodes 26, and/or an electrode of IMD 16 (e.g., a case electrode or can electrode). In some examples, each respective representation of electrical signals of the plurality of representations of electrical signals is associated with a respective electrode combination of the plurality of electrodes.

IMD 16 may be configured to deliver electrical stimulation to the particular patient via the clinician selected electrode combination. As one example, where a clinician selects the electrode combination, the clinician may select the therapy to deliver electrical stimulation to the particular patient via the selected electrode combination. As yet another example, the clinician may input the selected electrode combination to programmer 14 such that programmer 14 automatically selects a therapy and configures IMD 16 to deliver electrical stimulation to the particular patient via the selected electrode combination. As yet another example, the clinician may use a computing device to select an electrode combination that may be communicated to programmer 14 that may configure IMD 16 to deliver electrical stimulation to the particular patient via the clinician-selected electrode combination.

Figure 2:
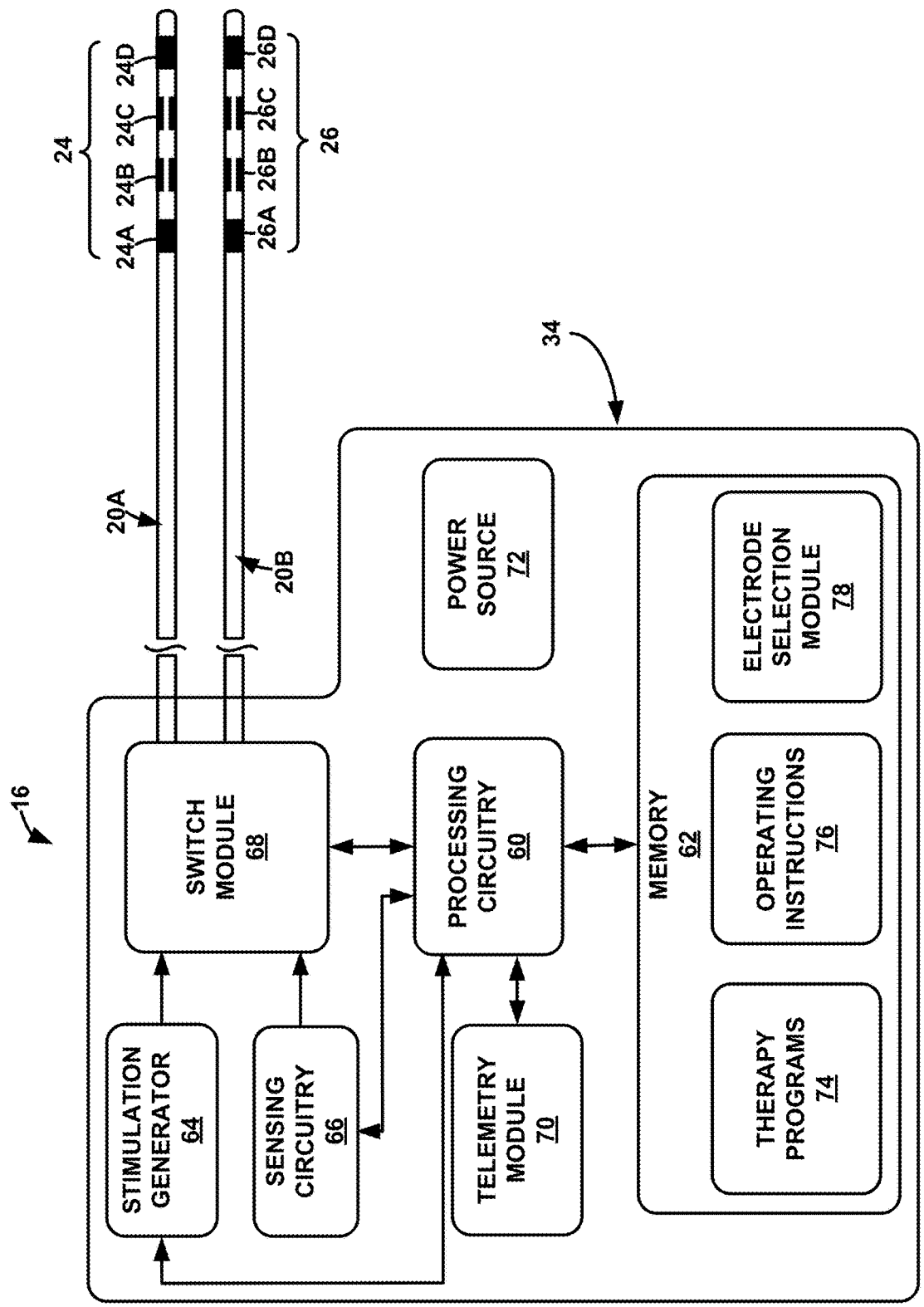
FIG. 2 is functional block diagram illustrating components of an example medical device.

FIG. 2 is functional block diagram illustrating components of an example IMD 16. In the example shown in FIG. 2, IMD 16 includes processing circuitry 60, memory 62, stimulation generator 64, sensing circuitry 66, switch module 68, telemetry module 70, and power source 72. Memory 62, as well as other memories described herein, may include any volatile or non-volatile media, such as a random-access memory (RAM), read only memory (ROM), non-volatile RAM (NVRAM), electrically erasable programmable ROM (EEPROM), flash memory, and the like. Memory 62 may store computer-readable instructions that, when executed by processing circuitry 60, cause IMD 16 to perform various functions described herein.

In the example shown in FIG. 2, memory 62 may store therapy programs 74, operating instructions 76, and electrode selection module 78, e.g., in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width, and pulse rate of a stimulation signal. Each stored therapy program 74 may also be referred to as a set of stimulation parameter values. Operating instructions 76 guide general operation of IMD 16 under control of processing circuitry 60 and may include instructions for monitoring brain signals within one or more brain regions via electrodes 24, 26 and delivering electrical stimulation therapy to patient 12. As discussed in further detail below and in accordance with one or more techniques of this disclosure, in some examples, memory 62 may store electrode selection module 78, that may include instructions that are executable by processing circuitry 60 to select one or more electrodes to sense electrical stimulation. For instance, electrode selection module 78 may be executable by processing circuitry 60 to select one or more electrode combinations of electrodes 24 and/or electrodes 26 to sense physiological signals and/or deliver electrical stimulation in accordance with the techniques of FIG. 4.

Stimulation generator 64, under the control of processing circuitry 60, generates stimulation signals for delivery to patient 12 via selected combinations of electrodes 24, 26. In some examples, stimulation generator 64 generates and delivers stimulation signals to one or more target regions of brain 28 (FIG. 1), via a selected electrode combination from electrodes 24, 26, based on one or more stored therapy programs 74. In some examples, therapy programs 74 are chosen at external programmer 14 and/or an external computer and transferred to IMD 16 and stored in memory 62. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processors described in this disclosure, including processing circuitry 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processing circuitry 60 is configured to control stimulation generator 64 according to therapy programs 74 stored by memory 62 to apply particular stimulation parameter values specified by one or more programs, such as amplitude, pulse width, and pulse rate.

In the example shown in FIG. 2, the set of electrodes 24 of lead 20A includes electrodes 24A-24D, and the set of electrodes 26 of lead 20B includes electrodes 26A-26D. Processing circuitry 60 may control switch module 68 to apply the stimulation signals generated by stimulation generator 64 to a selected electrode combination from electrodes 24 and/or electrodes 26. In particular, switch module 68 may couple stimulation signals to selected conductors within leads 20, that, in turn, deliver the stimulation signals across selected electrodes 24 and/or electrodes 26. Switch module 68 may be a switch array, switch matrix, multiplexer, or any other type of switching module configured to selectively couple stimulation energy to selected electrodes 24 and/or electrodes 26 and to selectively sense bioelectrical brain signals with selected electrodes 24 and/or electrodes 26. Hence, stimulation generator 64 is coupled to electrodes 24 and/or electrodes 26 via switch module 68 and conductors within leads 20. In some examples, however, IMD 16 does not include switch module 68. For instance, in some examples, IMD 16 may include individual voltage or current sources coupled to each electrode (i.e., a separate voltage and/or current source for each of electrodes 24 and/or electrodes 26).

As discussed above, processing circuitry 60 may control switch module 68 to apply the stimulation signals generated by stimulation generator 64, or sense electrical signals by sensing circuitry 66, to a selected electrode combination of electrodes 24 and/or electrodes 26. In some examples, the selected electrode combination of electrodes 24 and/or electrodes 26 may be unipolar. For instance, a unipolar selected combination may include one electrode of either electrodes 24 or electrodes 26 in combination with an electrode on the housing of IMD 16 (i.e., case or can), where one is an anode and the other is a cathode. In some examples, the selected electrode combination of electrodes 24 and/or electrodes 26 may be bipolar. As one example, a bipolar selected combination may include two electrodes from electrodes 24, where one is an anode and the other is a cathode. As another example, a bipolar selected combination may include two electrodes from electrodes 26, where one is an anode and the other is a cathode. As another example, a bipolar selected combination may include an electrode from electrodes 24 and an electrode from electrodes 26, where one is an anode and the other is a cathode. In some examples, the selected electrode combination of electrodes 24 and/or electrodes 26 may be multipolar. As one example, a multipolar selected combination may include multiple anodes and/or multiple cathodes selected from electrodes 24. As another example, a multipolar selected combination may include multiple anodes and/or multiple cathodes selected from electrodes 26. As one example, a multipolar selected combination may include multiple anodes and/or multiple cathodes selected from electrodes 24 and electrodes 26.

Stimulation generator 64 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing circuitry 66, under the control of processing circuitry 60, is configured to sense bioelectrical brain signals of patient 12 via a selected subset of electrode combinations with one or more electrodes 24 and/or electrodes 26 and at least a portion of a conductive outer housing 34 of IMD 16, an electrode on an outer housing of IMD 16 or another reference. Processing circuitry 60 may control switch module 68 to electrically connect sensing circuitry 66 to selected electrodes 24 and/or electrodes 26. In this way, sensing circuitry 66 may selectively sense bioelectrical brain signals with different combinations of electrodes 24 and/or electrodes 26 (and/or a reference other than an electrode of electrodes 24 and/or electrodes 26).

Although sensing circuitry 66 is incorporated into a common housing 34 with stimulation generator 64 and processing circuitry 60 in FIG. 2, in other examples, sensing circuitry 66 is in a separate outer housing from outer housing 34 of IMD 16 and communicates with processing circuitry 60 via wired or wireless communication techniques.

Telemetry module 70 is configured to support wireless communication between IMD 16 and an external programmer 14 or another computing device under the control of processing circuitry 60. Processing circuitry 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62, as discussed above. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
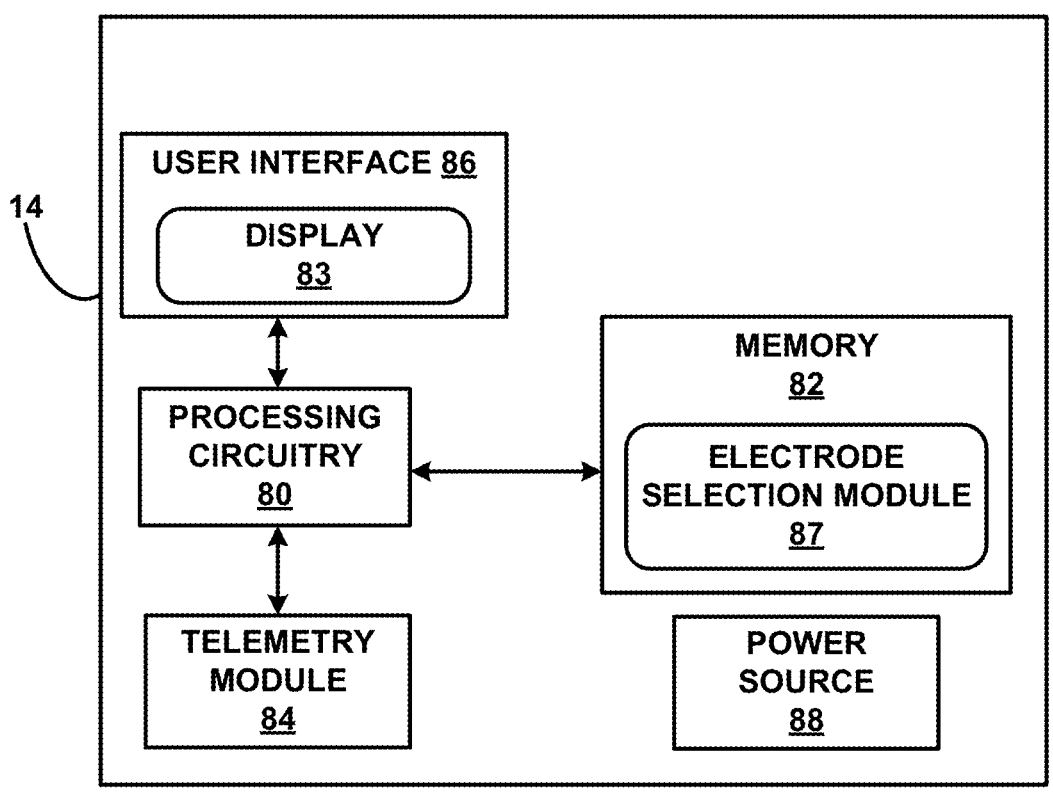
FIG. 3 is a functional block diagram illustrating components of an example medical device programmer.

FIG. 3 is a functional block diagram illustrating components of an example medical device programmer 14 (FIG. 1). In the example of FIG. 3, programmer 14 includes processing circuitry 80, memory 82, telemetry module 84, user interface 86 with display 83, and power source 88. Processing circuitry 80 controls user interface 86 and telemetry module 84 and stores and retrieves information and instructions to and from memory 82. Programmer 14 may be configured for use as a clinician programmer or a patient programmer. Processing circuitry 80 may comprise any combination of one or more processors including one or more microprocessors, DSPs, ASICs, FPGAs, or other equivalent integrated or discrete logic circuitry. Accordingly, processing circuitry 80 may include any suitable structure, whether in hardware, software, firmware, or any combination thereof, to perform the functions ascribed herein to processing circuitry 80.

A user, such as a clinician or patient 12, may interact with programmer 14 through user interface 86. User interface 86 includes a display 83, such as an LCD or LED display or other type of screen, with which processing circuitry 80 may present information related to the therapy (e.g., electrode combinations and associated therapeutic windows) and sensed electrical signals. In addition, user interface 86 may include an input mechanism to receive input from the user. The input mechanisms may include, for example, any one or more of buttons, a keypad (e.g., an alphanumeric keypad), a peripheral pointing device, a touch screen for display 83, or another input mechanism that allows the user to navigate through user interfaces presented by processing circuitry 80 of programmer 14 and provide input. In other examples, user interface 86 also includes audio circuitry for providing audible notifications, instructions or other sounds to patient 12, receiving voice commands from patient 12, or both.

Memory 82 may include instructions for operating user interface 86 and telemetry module 84, and for managing power source 88. In the example shown in FIG. 3, memory 82 also stores electrode selection module 87. Electrode selection module 87 may be similar to electrode selection module 78 of FIG. 2. As discussed in further detail below and in accordance with one or more techniques of this disclosure, in some examples, memory 82 of programmer 14 may store electrode selection module 87, that may include instructions that are executable by processing circuitry 80 to select one or more electrodes, and electrode combinations to sense electrical signals. For instance, electrode selection module 87 may be executable by processing circuitry 80 to select one or more of electrodes and electrode combinations to sense electrical signals in accordance with the techniques described below.

In some examples, patient 12, a clinician or another user may interact with user interface 86 of programmer 14 in other ways to manually select therapy programs, or combinations of electrodes, generate new therapy programs, modify therapy programs, transmit the new programs to IMD 16, or any combination thereof.

Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

While various information is illustrated and described as stored in memory 82 of programmer 14, it will be understood that some or all of this information may alternatively or additionally be stored within memory 62 of IMD 16. Moreover, at least some of the functionality ascribed to processing circuitry 80 of programmer 14 may instead or additionally be ascribed to processing circuitry 60 of IMD as discussed below (and vice versa).

Figure 4A:
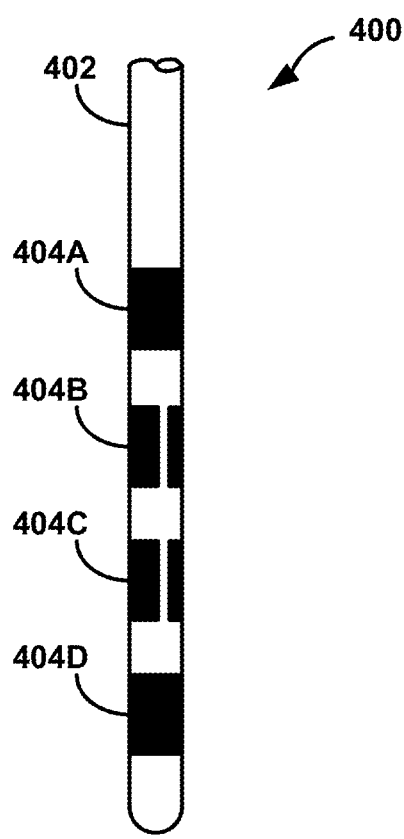
Figure 4B:
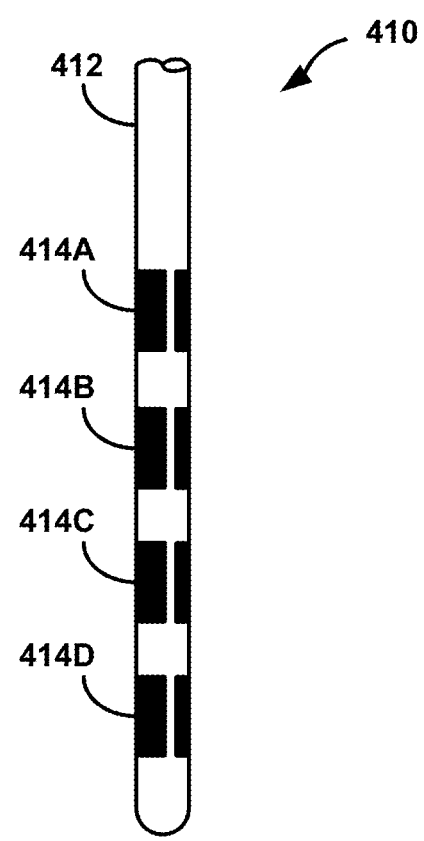

FIGS. 4A and 4B are conceptual diagrams of example leads 400 and 410, respectively, with respective electrodes carried by the lead. As shown in FIGS. 4A and 4B, leads 400 and 410 are example configurations that may be similar to leads 20 shown in FIG. 1. As shown in FIG. 4A, lead 400 includes four electrode levels 404 (includes levels 404A-404D) mounted at various lengths of lead housing 402. Lead 400 is inserted into through cranium 32 to a target position within brain 28.

Lead 400 is implanted within brain 28 at a location determined by the clinician to be near an anatomical region to be stimulated. Electrode levels 404A, 404B, 404C, and 404D may be equally spaced along the axial length of lead housing 402 at different axial positions. Each electrode level 404 may have one, two, three, or more electrodes located at different angular positions around the circumference (e.g., around the perimeter) of lead housing 402. As shown in FIG. 4A, electrode level 404A and 404D include a single respective ring electrode, and electrode levels 404B and 404C each include three electrodes at different circumferential positions. This electrode pattern may be referred to as a 1-3-3-1 lead in reference to the number of electrodes from the proximal end to the distal end of lead 400. Although the electrode levels are arranged as a 1-3-3-1 configuration, other configurations are possible as well, such as 1-1-3-3, 3-3-1-1, 1-3-1-3, 3-1-3-1, 1-3-3-3, or 3-3-3-1. Electrodes of one circumferential location may be lined up on an axis parallel to the longitudinal axis of lead 400. Alternatively, electrodes of different electrode levels may be staggered around the circumference of lead housing 402 such that electrodes on one level are offset circumferentially from electrodes on an adjacent level, as shown in FIGS. 4C and 4D. In this manner, the electrodes from one level may have circumferential positions slightly offset or fully offset (e.g., alternating) from the circumferential positions of electrodes at an adjacent level above and/or below the level. In addition, lead 400 or 410 may include asymmetrical, or unequally spaced, electrode locations around the circumference, or perimeter, of each lead or electrodes of the same level that have different sizes. These electrodes may include semi-circular electrodes that may or may not be circumferentially aligned between electrode levels.

Lead housing 402 may include one or more radiopaque stripes or other radiopaque orientation markers (not shown) along the outside of the lead housing. The radiopaque stripe corresponds to a certain circumferential location that allows lead 400 to the imaged when implanted in patient 12. Using the images of patient 12, the clinician can use the radiopaque stripe as a marker for the exact orientation of lead 400 within the brain of patient 12. Orientation of lead 400 may be needed to easily program the stimulation parameters by generating the correct electrode configuration to match the stimulation field defined by the clinician. In other examples, a marking mechanism other than a radiopaque stripe may be used to identify the orientation of lead 400. These marking mechanisms may include something similar to a tab, detent, or other structure on the outside of lead housing 402. In some examples, the clinician may note the position of markings along a lead wire during implantation to determine the orientation of lead 400 within patient 12.

FIG. 4B illustrates lead 410 that includes multiple electrodes at different respective circumferential positions at each of levels 414A-414D. Similar to lead 400, lead 410 is inserted through a burr hole in cranium 32 to a target location within brain 28. Lead 410 includes lead housing 412. Four electrode levels 414 (414A-414D) are located at the distal end of lead 410. Each electrode level 414 is evenly spaced from the adjacent electrode level and includes two or more electrodes. In one example, each electrode level 414 includes three, four, or more electrodes distributed around the circumference of lead housing 412. Therefore, lead 410 includes electrodes 414. Each electrode may be substantially rectangular in shape. Alternatively, the individual electrodes may have alternative shapes, e.g., circular, oval, triangular, rounded rectangles, or the like.

In alternative examples, electrode levels 404 or 414 are not evenly spaced along the longitudinal axis of the respective leads 400 and 410. For example, electrode levels 404C and 404D may be spaced approximately 3 millimeters (mm) apart while electrodes 404A and 404B are 10 mm apart. Variable spaced electrode levels may be useful in reaching target anatomical regions deep within brain 28 while avoiding potentially undesirable anatomical regions. Further, the electrodes in adjacent levels need not be aligned in the direction as the longitudinal axis of the lead, and instead may be oriented diagonally with respect to the longitudinal axis.

Leads 400 and 410 are substantially rigid to prevent the implanted lead from varying from the expected lead shape. Leads 400 or 410 may be substantially cylindrical in shape. In other examples, leads 400 or 410 may be shaped differently than a cylinder. For example, the leads may include one or more curves to reach target anatomical regions of brain 28. In some examples, leads 400 or 410 may be similar to a flat paddle lead or a conformable lead shaped for patient 12. Also, in other examples, leads 400 and 410 may any of a variety of different polygonal cross sections (e.g., triangle, square, rectangle, octagonal, etc.) taken transverse to the longitudinal axis of the lead.

As shown in the example of lead 400, the plurality of electrodes of lead 400 includes a first set of three electrodes disposed at different respective positions around the longitudinal axis of the lead and at a first longitudinal position along the lead (e.g., electrode level 404B), a second set of three electrodes disposed at a second longitudinal position along the lead different than the first longitudinal position (e.g., electrode level 404C), and at least one ring electrode disposed at a third longitudinal position along the lead different than the first longitudinal position and the second longitudinal position (e.g., electrode level 404A and/or electrode level 404D). In some examples, electrode level 404D may be a bullet tip or cone shaped electrode that covers the distal end of lead 402. Although lead 400 with circumferentially aligned electrode levels is generally used for the example systems and techniques described herein, other leads, such as lead 410 or leads 420 or 430 (which include circumferentially offset electrode levels) may similarly be employed for the techniques described herein with respect to sensing electrical signals and/or delivering electrical stimulation.

FIGS. 4C and 4D are conceptual diagrams of example leads 420 and 430, respectively, with respective electrodes carried by the lead. As shown in FIGS. 4C and 4D, leads 420 and 430 are example configurations that may be similar to leads 400 and 410, respectively, shown in FIGS. 4A and 4B. However, leads 420 and 430 include electrodes at offset circumferential positions between different levels of electrodes.

As shown in FIG. 4C, lead 420 includes four electrode levels 424 (includes levels 424A-424D) mounted at various lengths of lead housing 422. Lead 420 is configured to be inserted into through cranium 32 to a target position within brain 28. Electrode levels 424A, 424B, 424C, and 424D may be equally spaced along the axial length of lead housing 422 at different axial positions. Each electrode levels 424 may have one, two, three, or more electrodes located at different angular (or circumferential) positions around the circumference (e.g., around the perimeter) of lead housing 422. As shown in FIG. 4C, electrode level 424A and 424D include a single respective ring electrode, and electrode levels 424B and 424C each include three electrodes at different circumferential positions. This electrode pattern may be referred to as a 1-3-3-1 lead in reference to the number of electrodes from the proximal end to the distal end of lead 420. The circumferential locations of one electrode level (e.g., electrode level 424B) are offset, or staggered, from the circumferential locations of another electrode level (e.g., electrode level 424C). In this manner, the electrodes from one electrode level may have circumferential positions slightly offset or fully offset (e.g., alternating) from the circumferential positions of electrodes at an adjacent level above and/or below the level. Electrodes from one electrode level may be considered fully offset from electrodes of a different electrode level when the center positions of the electrodes at one electrode level are circumferentially equidistant from the center positions of the electrodes at a different level. Electrodes from one electrode level may be considered slightly or partially offset from electrodes of a different electrode level when the center positions of the electrodes at one electrode level are not circumferentially equidistant from the center positions of the electrodes at a different level. In this manner, lead 420 may include asymmetrical, or unequally spaced, electrode locations around the circumference, or perimeter, of each lead or electrodes of the same level that have different sizes. These electrodes may include semicircular electrodes that may or may not be circumferentially aligned between electrode levels. Circumferentially offset electrode levels may be beneficial for reducing sensing "blind spots" that may otherwise occur between electrode levels with circumferentially aligned electrodes.

FIG. 4D illustrates lead 430 that includes multiple electrodes at different respective circumferential positions at each of levels 434A-434D. Lead 430 may be similar to lead 420. Lead 430 is configured to be inserted through a burr hole in cranium 32 to a target location within brain 28. Lead 430 includes lead housing 432. Four electrode levels 434 (434A-434D) are located at the distal end of lead 430. Each electrode level 434 is evenly spaced from the adjacent electrode level and includes two or more electrodes. In one example, each electrode level 434 includes three, four, or more electrodes distributed around the circumference of lead housing 432. Therefore, lead 430 includes electrodes 434. Each electrode may be substantially rectangular in shape. Alternatively, the individual electrodes may have alternative shapes, e.g., circular, oval, triangular, rounded rectangles, or the like.

Each electrode levels 434 may have one, two, three, or more electrodes located at different angular (or circumferential) positions around the circumference (e.g., around the perimeter) of lead housing 432. The circumferential locations of one or more electrode levels (e.g., electrode levels 434B and 434D) are offset, or staggered, from the circumferential locations of other electrode levels (e.g., electrode levels 434A and 434C). In this manner, the electrodes from one electrode level may have circumferential positions slightly offset or fully offset (e.g., alternating) from the circumferential positions of electrodes at an adjacent level above and/or below the level and/or other electrode levels of lead 430. In the example of FIG. 4D, the electrodes of electrode level 434A and 434C are circumferentially aligned, and the electrodes of electrode level 434B and 434D are circumferentially aligned. Although adjacent electrode levels have circumferentially offset electrodes, other leads may include adjacent electrode levels having circumferentially aligned electrodes and electrode levels with circumferentially offset electrodes even though the levels are separated by one or more electrode levels. Any combination of electrode levels with electrodes circumferentially aligned or circumferentially offset are contemplated. For example, each electrode level may include electrodes that are at least partially offset from the electrodes of every other electrode level. Lead 430 may include asymmetrical, or unequally spaced, electrode locations around the circumference, or perimeter, of each lead or electrodes of the same level that have different sizes. These electrodes may include semicircular electrodes that may or may not be circumferentially aligned between electrode levels. Circumferentially offset electrode levels may be beneficial for reducing sensing "blind spots" that may otherwise occur between electrode levels with circumferentially aligned electrodes.

In some examples, electrode levels 424 or 434 are not evenly spaced along the longitudinal axis of the respective leads 420 and 430. For example, electrode levels 424C and 424D may be spaced approximately 3 millimeters (mm) apart while electrodes 424A and 424B are 10 mm apart. Variable spaced electrode levels may be useful in reaching target anatomical regions deep within brain 28 while avoiding potentially undesirable anatomical regions. Further, the electrodes in adjacent levels need not be aligned in the direction as the longitudinal axis of the lead, and instead may be oriented diagonally with respect to the longitudinal axis.

As shown in the example of lead 420, the plurality of electrodes of lead 420 includes a first set of three electrodes disposed at different respective positions around the longitudinal axis of the lead and at a first longitudinal position along the lead (e.g., electrode level 424B), a second set of three electrodes disposed at a second longitudinal position along the lead different than the first longitudinal position and at circumferential positions different than the electrodes of electrode level 424B (e.g., electrode level 424C), and at least one ring electrode disposed at a third longitudinal position along the lead different than the first longitudinal position and the second longitudinal position (e.g., electrode level 424A and/or electrode level 424D). In some examples, electrode level 424D may be a bullet tip or cone shaped electrode that covers the distal end of lead 420.

Figure 5A:
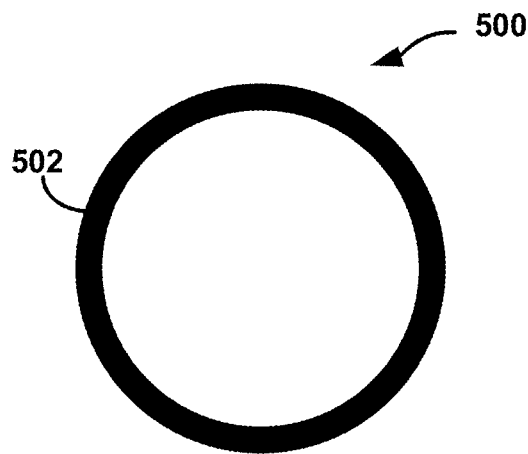
FIGS. 5A, 5B, 5C, and 5D are conceptual diagrams of example electrodes disposed around a perimeter of a lead at a particular longitudinal location.

FIGS. 5A-5D are transverse cross-sections of example stimulation leads having one or more electrodes around the circumference of the lead. As shown in FIGS. 5A-5D, one electrode level, such as one of electrode levels 404 and 414 of leads 400 and 410, are illustrated to show electrode placement around the perimeter, or around the longitudinal axis, of the lead. FIG. 5A shows electrode level 500 that includes circumferential electrode 502. Circumferential electrode 502 encircles the entire circumference of electrode level 500 and may be referred to as a ring electrode in some examples. Circumferential electrode 502 may be utilized as a cathode or anode as configured by the user interface.

Figure 5B:
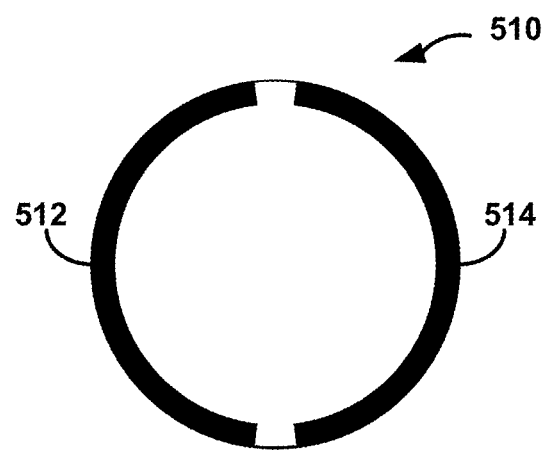

FIG. 5B shows electrode level 510 that includes two electrodes 512 and 514. Each electrode 512 and 514 wraps approximately 170 degrees around the circumference of electrode level 510. Spaces of approximately 10 degrees are located between electrodes 512 and 514 to prevent inadvertent coupling of electrical current between the electrodes. Smaller or larger spaces between electrodes (e.g., between 10 degrees and 30 degrees) may be provided in other examples. Each electrode 512 and 514 may be programmed to act as an anode or cathode.

Figure 5C:
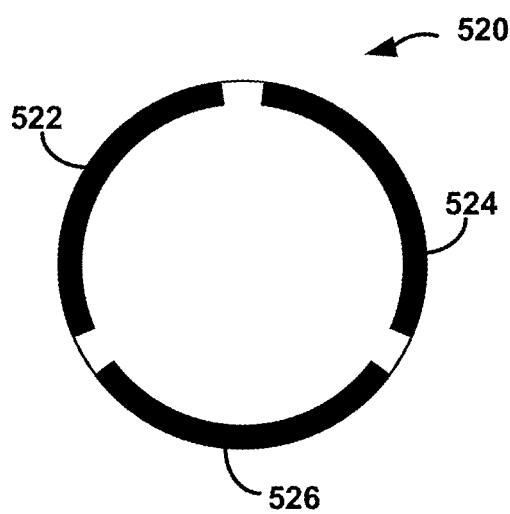

FIG. 5C shows electrode level 520 that includes three equally sized electrodes 522, 524 and 526. Each electrode 522, 524 and 526 encompass approximately 110 degrees of the circumference of electrode level 520. Similar to electrode level 510, spaces of approximately 10 degrees separate electrodes 522, 524 and 526. Smaller or larger spaces between electrodes (e.g., between 10 degrees and 30 degrees) may be provided in other examples. Electrodes 522, 524 and 526 may be independently programmed as an anode or cathode for stimulation.

Figure 5D:
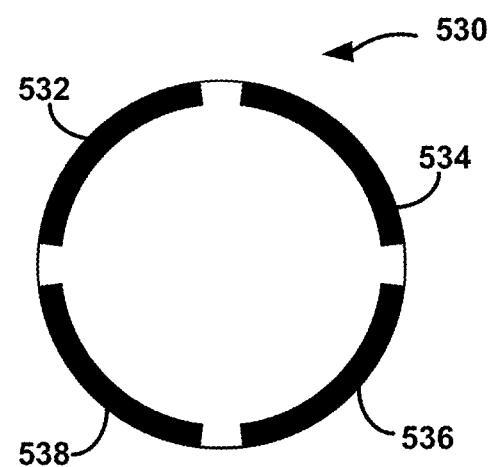

FIG. 5D shows electrode level 530 that includes four electrodes 532, 534, 536 and 538. Each electrode 532, 534, 536 and 538 covers approximately 80 degrees of the circumference with approximately 10 degrees of insulation space between adjacent electrodes. Smaller or larger spaces between electrodes (e.g., between 10 degrees and 30 degrees) may be provided in other examples. In other examples, up to ten or more electrodes may be included within an electrode level. In alternative examples, consecutive electrode levels of lead 20 may include a variety of electrode levels 500, 510, 520, and 530. For example, lead 20 (or any other lead described herein) may include electrode levels that alternate between electrode levels 510 and 530 depicted in FIGS. 5B and 5D. In this manner, various stimulation field shapes may be produced within brain 28 of patient 112. Further the above-described sizes of electrodes within an electrode level are merely examples, and the invention is not limited to the example electrode sizes.

Also, the insulation space, or non-electrode surface area, may be of any size. Generally, the insulation space is between approximately 1 degree and approximately 20 degrees. More specifically, the insulation space may be between approximately 5 and approximately 15 degrees. In other examples, insulation space may be between approximately 10 degrees and 30 degrees or larger. Smaller insulation spaces may allow a greater volume of tissue to be stimulated. In alternative examples, electrode size may be varied around the circumference of an electrode level. In addition, insulation spaces may vary in size as well. Such asymmetrical electrode levels may be used in leads implanted at tissues needing certain shaped stimulation fields.

Figure 6:
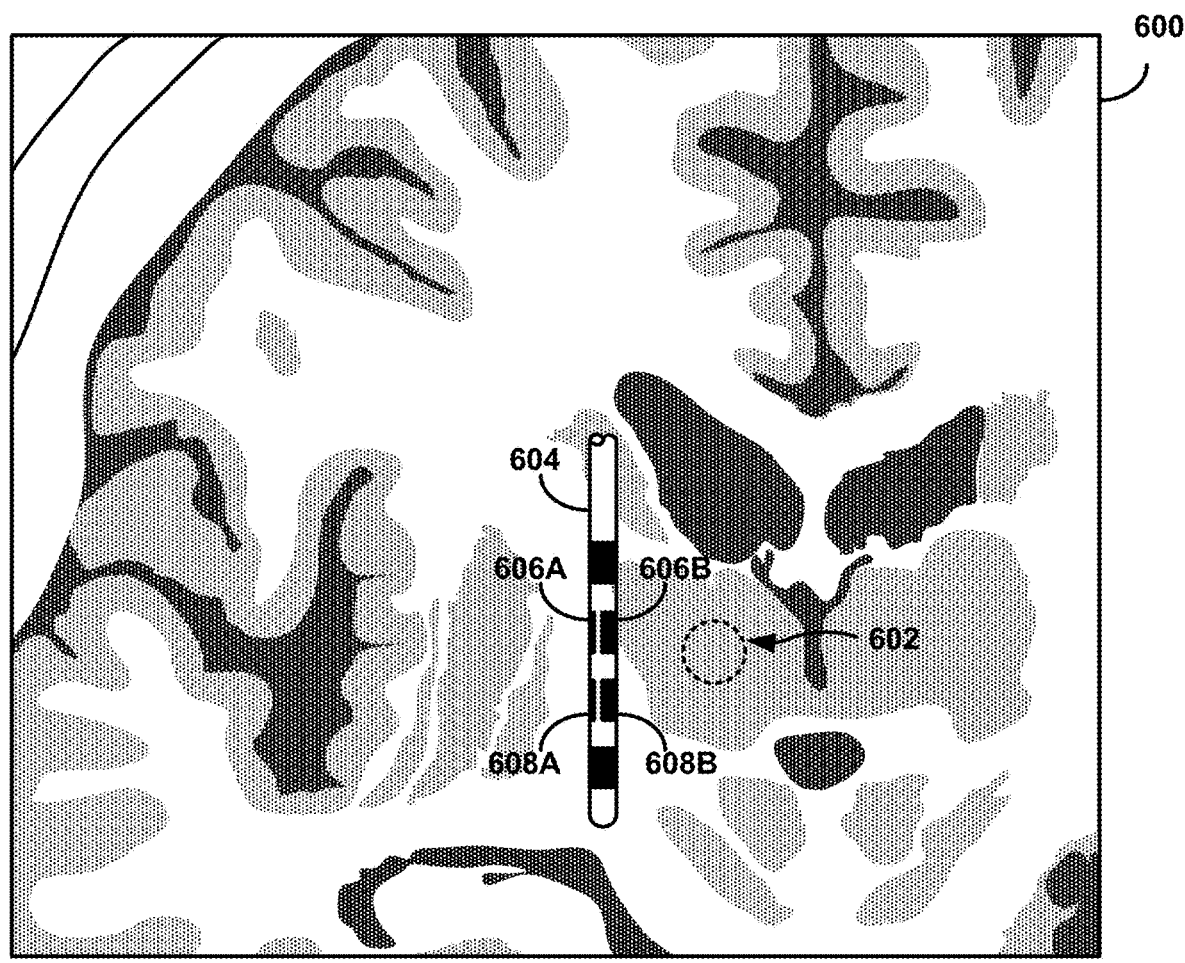
FIG. 6 is a coronal view of example tissue with a lead placed with respect to a target location within tissue.

FIG. 6 is a coronal view of example tissue with a lead 604 placed offset with respect to a target location within tissue. As shown in FIG. 6, a representation of anatomical regions of brain 28 is displayed by coronal view 600. Coronal view 600 is a front-back vertical section of brain 28. Coronal view 600 may be an actual image of brain 28 produced with magnetic resonance imaging (MRI), computed tomography (CT), or another imaging modality. Coronal view 600 may be an illustration of the location of a lead with respect to a target tissue from which electrical signals originate (e.g., LFP signals). In some examples, coronal view 600 may be presented by programmer 14, for example on display 83, or another device to indicate the relative position of lead 604 and the electrodes carried by the lead according to the sensed electrical signals. These images thus may be used to produce the anatomical regions needed to help the clinician program the stimulation parameters.

Coronal view 600 is a 2D coronal slice of brain 28. Differently shaded portions of coronal view 600 indicate varying densities of tissue within brain 28. Darker portions indicate less dense tissue. For example, the darkest portion of coronal view 600 is indicative of spaces within brain 28 that contain cerebral spinal fluid (CSF). White portions of brain 28 indicate dense tissue and more neurons. It should be noted that coronal view 600 is only an example, and actual images may include a wider range of shades and higher image resolution. Coronal view 600 provides a first perspective of the lead and the anatomical region in which the lead is implanted.

As shown in FIG. 6, lead 604 may be a lead icon that represents an actual lead implanted within patient 12. Lead 604 includes electrodes such as electrodes 606A and 606B located at the same longitudinal position and different circumferential positions around the perimeter of lead 604. Electrode 606C cannot be seen because it is located in the backside of lead 604. Similarly, lead 604 includes electrodes such as electrodes 608A and 608B located at the same longitudinal position and different circumferential positions around the perimeter of lead 604. Electrode 608C cannot be seen because it is located on the backside of lead 604. When electrical signals, such as LFP signals originate from target tissue 602, the largest amplitude and power of the signal will likely be sensed by the electrode or electrodes closest to target tissue 602. In this example, a sensing electrode combination 606B and 608B may sense a larger amplitude electrical signal from target tissue 602 than any other electrode combinations on lead 604. In some examples, monopolar sensing may result in electrode 606B sensing the highest amplitude of electrical signals from target tissue 602. If lead 604 moves with respect to tissue, a different electrode, such as electrode 606A (for lead rotation) or electrode 608B (for longitudinal lead movement), may not sense electrical signals with the largest amplitude.

Leads, such as lead 604, may be offset from a signal-source, such as target tissue 602. As stated above, lead 604 is offset from the signal-source so that electrodes 606A, 606B, 608A and 608B are all implanted at a distance from the signal-source. This offset may enable identification of the direction of the signal-source because different electrodes are different distances from the signal-source due to their respective locations along the lead. In examples of the present disclosure, target tissue 602 may be within the dorsal STN.

Figure 7:
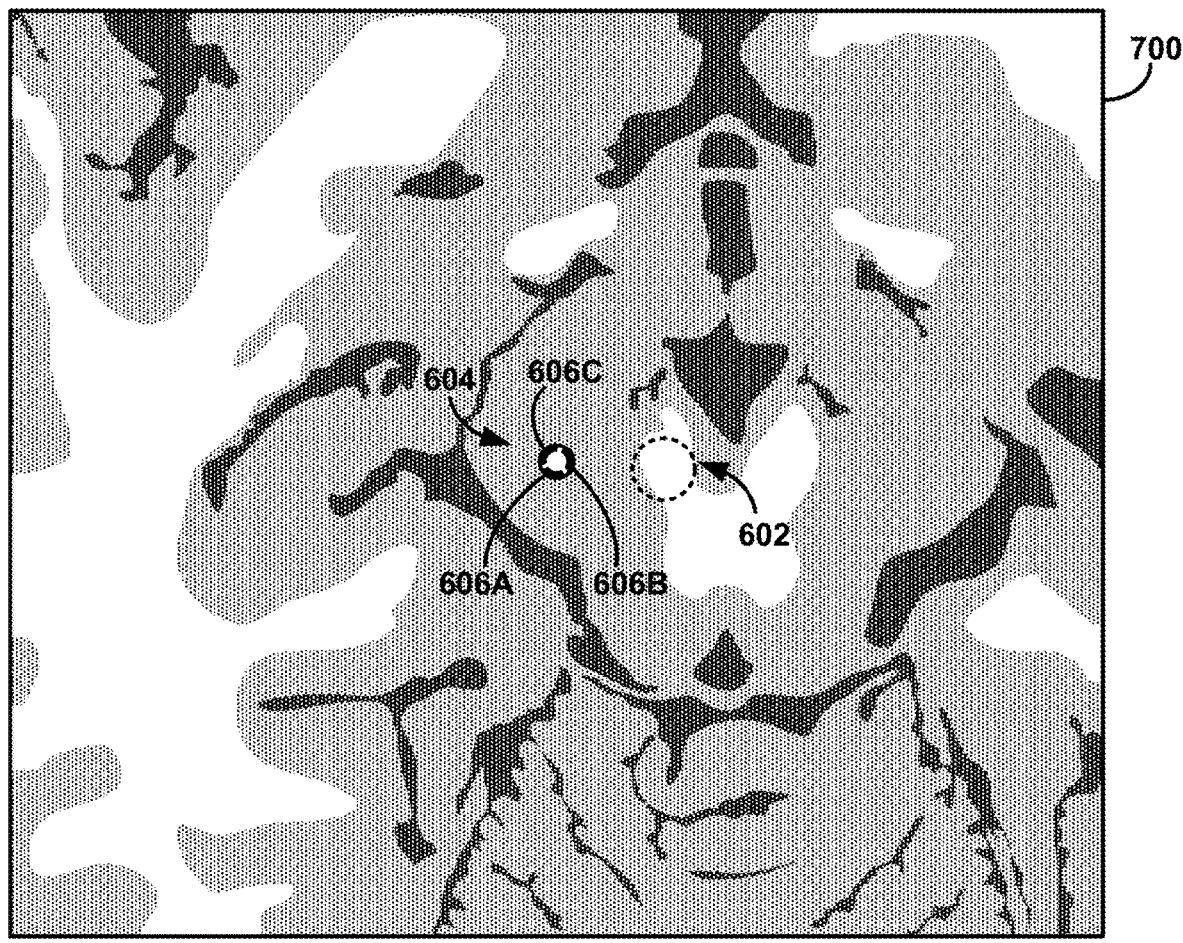
FIG. 7 is an axial view of example tissue with a lead placed with respect to a target location within tissue.

FIG. 7 is an axial view of example tissue with a lead 604 placed with respect to a target tissue 602. Axial view 700 is a different view of tissue than coronal view 600. Axial view 700 also shows the cross-sectional view of lead 604 and electrodes 606A, 606B, and 606C. As shown in axial view 700, electrode 606B is closest to target tissue 602 and may register the largest amplitude of sensed electrical signals when compared to the remaining electrodes of lead 604. If lead 604 were to rotate within tissue due to patient movement, lead pull, or some other force, a different electrode, such as electrode 606A, may be located closest to target tissue 602 and sense electrical signals with the largest amplitude when compared to other electrodes. Although FIGS. 6 and 7 discuss electrical signals that may originate in tissue, the same spatial origin may be used when sensing electrical signals evoked from delivered stimulation or sensing delivered stimulation itself for determining lead movement.

Figure 8:
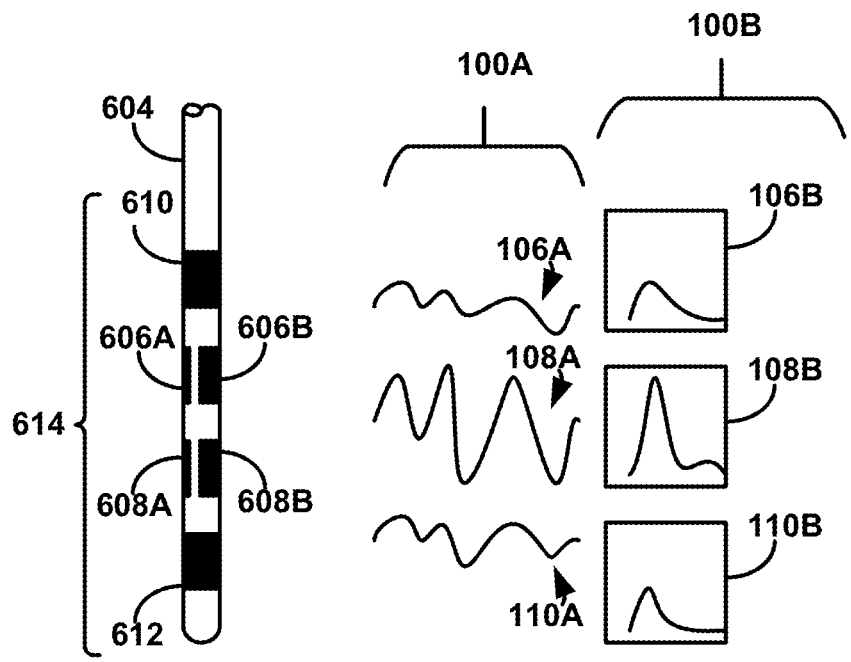
FIG. 8 is a conceptual diagram of example waveform amplitudes sensed by electrode combinations located at different axial positions along the length of a medical lead in accordance with one or more techniques of this disclosure.

As shown in the example of FIG. 8, waveform amplitudes 106A, 108A, and 110A (collectively "waveform amplitudes 100A") are examples of electrical signal information from respective electrode combinations of lead 604. Spectral powers 106B, 108B, and 110B (collectively "spectral powers 100B") are additional, or alternative, examples of electrical signal information. Each of waveform amplitudes 100A and spectral powers 100B may be determined from electrical signals sensed by a respective electrode combination. Further, spectral powers 100B may be represented in a similar manner to that of FIG. 8 on display 83 (FIG. 3) to a clinician during an electrode combination selection process. That is to say, in one example, spectral powers 100B may also be represented by display 83 for a clinician to observe spectral powers 100B of waveform amplitudes 100A.

Waveform amplitude 106A may be sensed between electrodes 610 and 606A, 606B and 606C (not shown in FIG. 8). Since the waveform amplitude 106A is being sensed between two axial levels, impedance may need to be matched as closely as possible in order to ensure the best quality representation of waveform amplitude 106A. Impedance matching is the practice of designing the input impedance of an electrical load or the output impedance of its corresponding signal source to maximize the power transfer or minimize signal reflection from the load.

As shown, electrode 610 has a greater surface area than electrodes 606A, 606B and 606C separately. Electrode 610 may thus have a lower resistivity (e.g., impedance, if the electrodes are made of the same material or have the same surface texture or coating) than the resistivity of each of electrodes 606A, 606B and 606C individually. Put differently, each of electrodes 606A, 606B and 606C have smaller cross-sectional areas than the cross-sectional area of electrode 610, and thus have a higher resistivity and higher impedance. However, by combining electrodes 606A, 606B and 606C together with a common polarity to act as one "ring" electrode for the purpose of sensing waveform amplitude 106A, the impedances between different levels of electrodes can be matched, or close to matched, and a better signal recorded. Thus, for purposes of discussion about sensing between axial combinations of electrodes, electrodes 606A, 606B and 606C can be electrically combined together to act as one electrode (collectively "electrode 606") and electrodes 608A, 608B and 608C can be combined together to act as one electrode (collectively "electrode 608"). It is noted that in other examples, signals may be sensed between a ring electrode any fewer than all of the electrodes at another axial location.

Waveform amplitude 108A may be sensed between electrode 606 and electrode 608 and spectral power 108B may be the spectral power representation of waveform amplitude 108A. Waveform amplitude 110A may be sensed between electrode 608 and electrode 612 and spectral power 110B may be the spectral power representation of waveform amplitude 110A.

Thus, as discussed above, waveform amplitudes may be sensed between electrode combination subset 614. Combination subset 614 may include:
 a. electrode 612 and electrode 608
 b. electrode 608 and electrode 606
 c. electrode 606 and electrode 610

Other combinations may be used, such as those combinations in which electrodes of the combination are separated by one or more levels. These combinations may be used if there were a problem with an electrode or multiple electrodes or to provide different electrical signal information. Such combination may be:
 a. electrode 612 and electrode 610
 b. electrode 612 and electrode 606
 c. electrode 608 and electrode 610

In some examples, axial sensing of waveform amplitude for spectral power may also be performed between the following electrode combinations and combination subset 614 may also include:
 a. electrode 606A and electrode 608A
 b. electrode 606B and electrode 608B
 c. electrode 606C and electrode 608C Measuring between electrode segments adjacent to each other is most common. However, in some examples it may be possible to sense between non-adjacent electrode segments. This may be desirable in the event an electrode or electrode segment is not functioning (e.g., an electrode fails an impedance test indicating a possible conductor break) or trying to match electrodes with more similar impedances (e.g., due to tissue surfaces or other impedance mismatching issues), for example. In another example, this approach may allow for more finely tuning the origin of the signal. In these examples, the following electrode combinations and combination subset may also include:
 a. electrode 606A and electrode 608B
 b. electrode 606A and electrode 608C
 c. electrode 606B and electrode 608A
 d. electrode 606B and electrode 608C
 e. electrode 606C and electrode 608A
 f. electrode 606C and electrode 608B In some examples, electrode combination subset 614 may also include waveform amplitudes sensed between any of electrodes 610, 612, 606, and 608 and an electrode on housing 34, such as a "can" electrode for unipolar sensing.

In an example of the present disclosure sensing circuitry 66 (FIG. 2) may be configured to sense electrical signals, such as waveform amplitudes 100A, from a plurality of electrode combinations. The plurality of electrode combinations may come from each electrode 612, 610, 608, and 606 carried by medical lead 604. Lead 604 comprises electrodes 612, 610, 608, and 606 located at different axial positions along a length of lead 614. Processing circuitry 60 (FIG. 2) may be configured to identify, based on sensed electrical signals, such as waveform amplitudes 100A, from electrode combination subset 614, an electrode combination associated with the largest amplitude or spectral power (e.g., in the Beta range). Each electrode combination of subset 614 may comprise electrodes located at different axial positions along the length of lead 604.

In FIG. 8, processing circuitry 66 (FIG. 2) has identified a plurality of electrode combinations within electrode subset 614 that a clinician or the processing circuitry 66 may choose from. In examples of the present disclosure, each spectral power 100B identified by processing circuitry 66 may be displayed on display 83 (FIG. 3) and a clinician may select an electrode combination providing a spectral power 100B showing the largest detection of waveform amplitudes 100A in an axial direction. For example, in FIG. 8, spectral power 108B shows the largest magnitude of power to frequency. Spectral power 108B is a representation of waveform 108A, which is sensed between electrodes 608 and 606. At display 83 (FIG. 3) a clinician may then select spectral power 108B as the strongest signal representation electrodes 606 and 608 are closest or at least sense waveform amplitude 100A from target tissue 602 the best between all electrode combinations from electrode combination subset 614. This selection, by the clinician, of electrodes 608 and 606 may be stored as the clinician's choice for an axial electrode combination providing a sensed axial direction to target tissue 602 (FIGS. 6 and 7).

Figure 9:
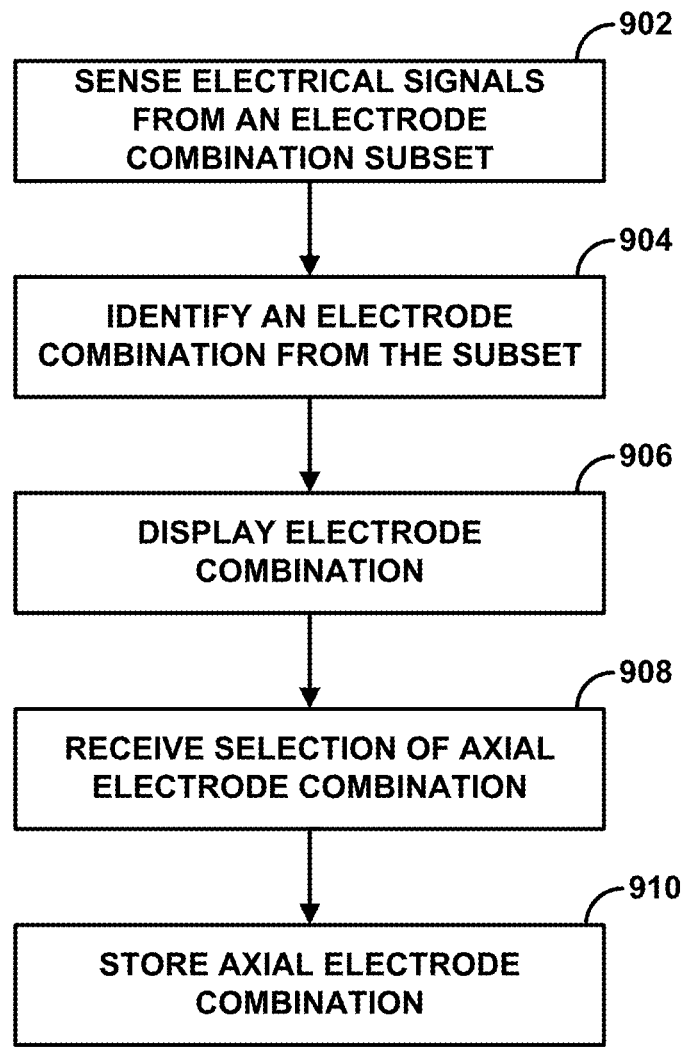
FIG. 9 is a flow diagram of an example technique for selecting an axial electrode combination, in accordance with one or more techniques of this disclosure.

FIG. 9 is a flow diagram of an example technique for selecting an axial electrode combination, in accordance with one or more techniques of this disclosure. Processing circuitry 80 of programmer 14 will be described for the example of FIG. 9, by any devices herein, or combinations of devices, may perform similar techniques of FIG. 9. As shown in the example of FIG. 9, programmer 14 may select an axial electrode combination. For example, sensing circuitry 66 may sense electrical signals from a subset of electrode combinations, such as waveform amplitudes 100A (902). As discussed above, each electrode 612, 610, 608, and 606 are located at different axial positions along a length of medical lead 604. Processing circuitry 60 (FIG. 2) may identify an electrode combination from subset of electrode combinations 614 based on sensed waveform amplitudes 100A (904).

Display 83 (FIG. 3) may show a representation of waveform amplitude 100A from the electrode combination (906). Waveform amplitude 100A may be displayed as a waveform amplitude as sensed by sensing circuitry 66. In another example, waveform amplitude 100A may be displayed as spectral power 100B. In another example, display 83 may show waveform amplitude 100A in a bar graph based upon strength of amplitude. A clinician may select a representation of waveform amplitude 100A displayed which correlate to the displayed electrode combination (908). For example, electrodes 608 and 610 as discussed in FIG. 8. Programmer 14 may store the axial electrode combination selected by the clinician for further reference when the clinician creates a stimulation therapy for patient 12 (910). In another example, the clinician may select more than one electrode combination. For example, if two or more spectral powers 100B are identical or similar, the clinician may want to store both to assist in their selection of the stimulation electrodes when viewed with all the electrode combination information at the end of the electrode selection process.

FIGS. 10A and 10B are a conceptual diagram of example waveform amplitudes sensed by electrode combinations located at different circumferential positions of a medical lead in accordance with one or more techniques of this disclosure.

As shown in the example of FIGS. 10A and 10B, waveform amplitudes 202A, 204A, 206A, 208A, 210A, and 212A (collectively "waveform amplitudes 200A") are examples of initial electrical signal information. Spectral powers 202B, 204B, 206B, 208B, 210B, and 212B (collectively "spectral powers 200B") are additional, or alternative, examples of initial electrical signal information. Each of waveform amplitudes 200A and spectral powers 200B may be determined from electrical signals sensed by a respective electrode combination. Further, spectral powers 200B may be represented in a similar manner on display 83 (FIG. 3) to that of FIGS. 10A and 10B to a clinician during an electrode combination selection process. That is to say, in one example, spectral powers 200B may also be represented by display 83 for a clinician to observe spectral powers 200B of waveform amplitudes 200A.

Waveform amplitude 202A may be sensed between electrodes 606A and 606B and spectral power 202B may be the spectral representation of waveform amplitude 202A. Waveform amplitude 204A may be sensed between electrodes 606B and 606C. Waveform amplitude 206A may be sensed between electrode 606C and electrode 606A and spectral power 206B may be the spectral power representation of waveform amplitude 206A. Waveform amplitude 208A may be sensed between electrode 608A and electrode 608B and spectral power 208B may be the spectral power representation of waveform amplitude 208A. Waveform amplitude 210A may be sensed between electrode 608B and electrode 608C and spectral power 210B may be the spectral power representation of waveform amplitude 210A. Waveform amplitude 212A may be sensed between electrode 608C and electrode 608A and spectral power 212B may be the spectral power representation of waveform amplitude 212A.

In an example of the present disclosure, sensing circuitry 66 (FIG. 2) may be configured to sense electrical signals, such as waveform amplitudes 200A, from a plurality of electrode combinations. Each electrode of the electrode combination subset 616 may be carried by lead 604. Lead 604 may comprise electrodes at different circumferential positions around a perimeter of lead 604. Processing circuitry 60 (FIG. 2) may be configured to identify, based on sensed electrical signals, such as waveform amplitudes 200A, from a second subset of electrode combinations 616, an electrode combination from the second subset of electrode combinations 616 comprising electrodes located at a same axial position and different circumferential positions around the perimeter of lead 604.

In FIGS. 10A and 10B, processing circuitry 66 (FIG. 2) has identified a plurality of electrode combinations within electrode subset 616. In examples of the present disclosure, each spectral power 200B identified by processing circuitry 66 may be displayed on display 83 (FIG. 3) and a clinician may select an electrode combination providing a spectral power 200B showing the spectral power 200B with the largest magnitude in a circumferential direction. For example, in FIGS. 10A and 10B, spectral power 206B shows the largest magnitude of power to frequency. Spectral power 206B is a representation of waveform 206A, which is sensed between electrodes 606A and 606C. At display 83 (FIG. 3) a clinician may then select spectral power 206B as the best representation of waveform amplitude 200A between all electrode combinations from electrode combination subset 616. This selection would of electrodes 606A and 606C may be stored as the clinician's choice for a circumferential electrode combination providing a sensed axial direction to target tissue 602 (FIGS. 6 and 7). The clinician, through the observation of spectral powers 206B and 204B may gain a directional knowledge of the direction of waveform amplitude 200A represented by arrow 620. In another example, programmer 14 may automatically select the electrode combination by evaluating and selecting the electrode combination automatically based upon the waveform amplitude 200A or the spectral power 200B or both. Programmer 14 may automatically evaluate each waveform amplitude 200A or each spectral power 200B and decide based upon the greatest spectral power sensed.

In another example, programmer 14 may attribute a direction (e.g. electrode 606A) to the target tissue 602. For example, spectral power 202B of waveform amplitude 202A between electrode 606A and 606B may be combined (e.g. summed) with spectral power 206B waveform amplitude 206A between 606A and 606C. The summed waveform amplitude showing 606A has the direction to use to stimulate target tissue 602. This example may also be extended around electrode 606. Combining 606A-606B with 606B-606C to represent the signal at 606B and combining 606B-606C with 606C-606A to represent 606C. This may also be extended for electrode 608 as well. This stratification may show a relative gradation, normalized rank, or ordinal rank to the electrodes. In another example, a clinician may even pick the directional segment with the strongest (or weakest) combined signal representation (e.g. if the resulting set of combinations results in 606A being the largest programmer 14 recommends electrode 606A). In this manner, the user interface may create a "heat map" or relative ranking of electrodes to be presented to a user. Programmer 14 may generate the heat map based on the differential amplitudes or spectral powers obtained from the differential recordings across electrodes. The heat map may provide a clear representation of which electrodes may be used for stimulation.

Figure 11:
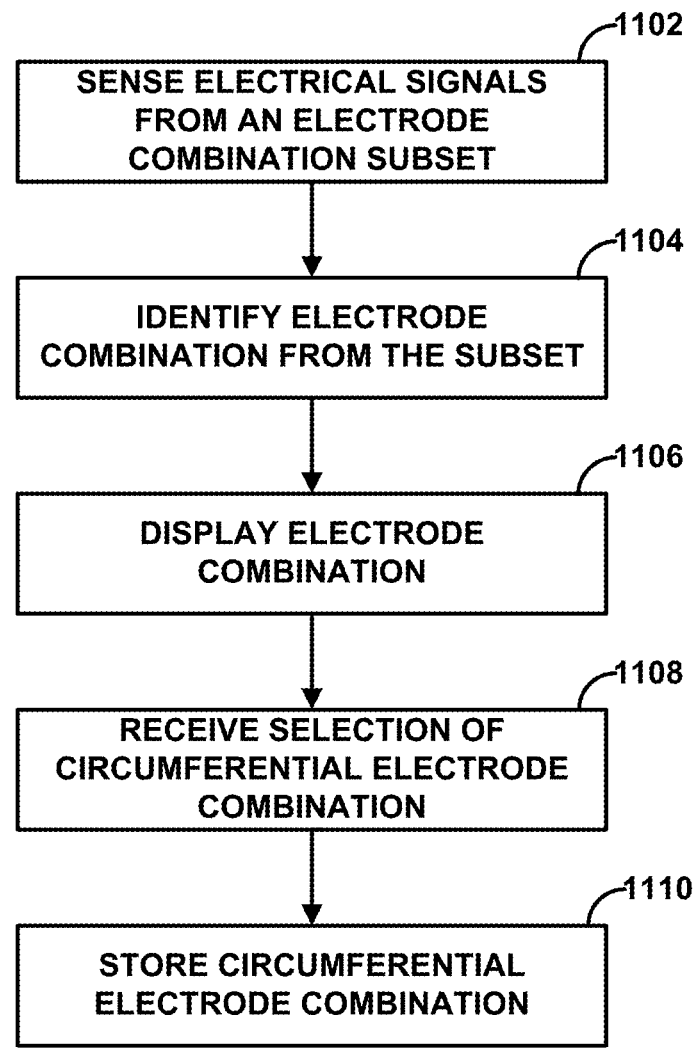
FIG. 11 is a flow diagram of an example technique for selecting a circumferential electrode combination, in accordance with one or more techniques of this disclosure.

FIG. 11 is a flow diagram of an example technique for selecting a circumferential electrode combination, in accordance with one or more techniques of this disclosure. In examples of the present disclosure, programmer 14 may select a circumferential electrode combination with sensing circuitry 66 (FIG. 2) based on electrical signals, such as waveform amplitudes 200A, from a plurality of electrode combinations, such as electrode combination subset 616 (1102). As discussed above, each electrode 606A, 606B, and 606C are located at different circumferential positions of medical lead 604, with electrodes 608A, 608B, and 608C having circumferential positions aligned with electrodes 606A, 606B, and 606C, respectively. In other examples, electrodes 606A, 606B, and 606C may be circumferentially offset (slightly offset or fully offset) from 608A, 608B, and 608C (e.g., as shown for lead 420 of FIG. 4C) such that all of electrodes 606A, 606B, 606C, 608A, 608B, and 608C are all disposed at unique and different circumferential positions around the lead. Processing circuitry 60 (FIG. 2) may identify an electrode combination of electrode combinations subset 616 based on sensed waveform amplitudes 200A (1104).

Display 83 (FIG. 3) may show a representation of a waveform amplitude 200A for the electrode combination (1106). Waveform amplitude 200A may be displayed as a waveform amplitude as sensed by sensing circuitry 66. In another example, waveform amplitude 200A may be displayed as spectral power 200B. In another example, display 83 may show waveform amplitude 200A in a bar graph based upon strength of amplitude. A clinician may select a representation of spectral power 200B displayed which correlate to an electrode combination of circumferential electrodes (1108). For example, electrodes 606A and 606C as discussed in FIGS. 10A and 10B. The circumferential electrode combination selected by the clinician may then be stored for further reference when the clinician creates a stimulation therapy for patient 12 (1110). In another example, the clinician may select more than one electrode combination. For example, if two or more spectral powers 200B are identical or similar, the clinician may want to store both to assist in their selection of the stimulation electrodes when viewed with all the electrode combination information at the end of the electrode selection process. In some examples, the electrode combination may include electrodes from different electrode levels that also have different circumferential positions. For example, the two electrodes of the electrode combination may be from respective electrode levels that have partially or fully offset circumferential positions.

In another example, programmer 14 may automatically select the circumferential electrode combination based upon the waveform amplitude 200A or the spectral power 200B or both. The automatic selection may be based upon the waveform amplitude 200A having the greatest amplitude or the spectral power 200B with the largest spectral power. In another example, programmer 14 may identify electrodes associated with the lowest spectral power. For example, the lowest spectral power may be indicative of white-matter tracts in the brain which tend to have very weak signals compared to the surrounding gray matter. In this manner, the electrodes associated with the lower spectral power may be selected to target stimulation to these white-matter tracks to treat conditions associated with dysfunction of these white-matter tracks.

Figure 12:
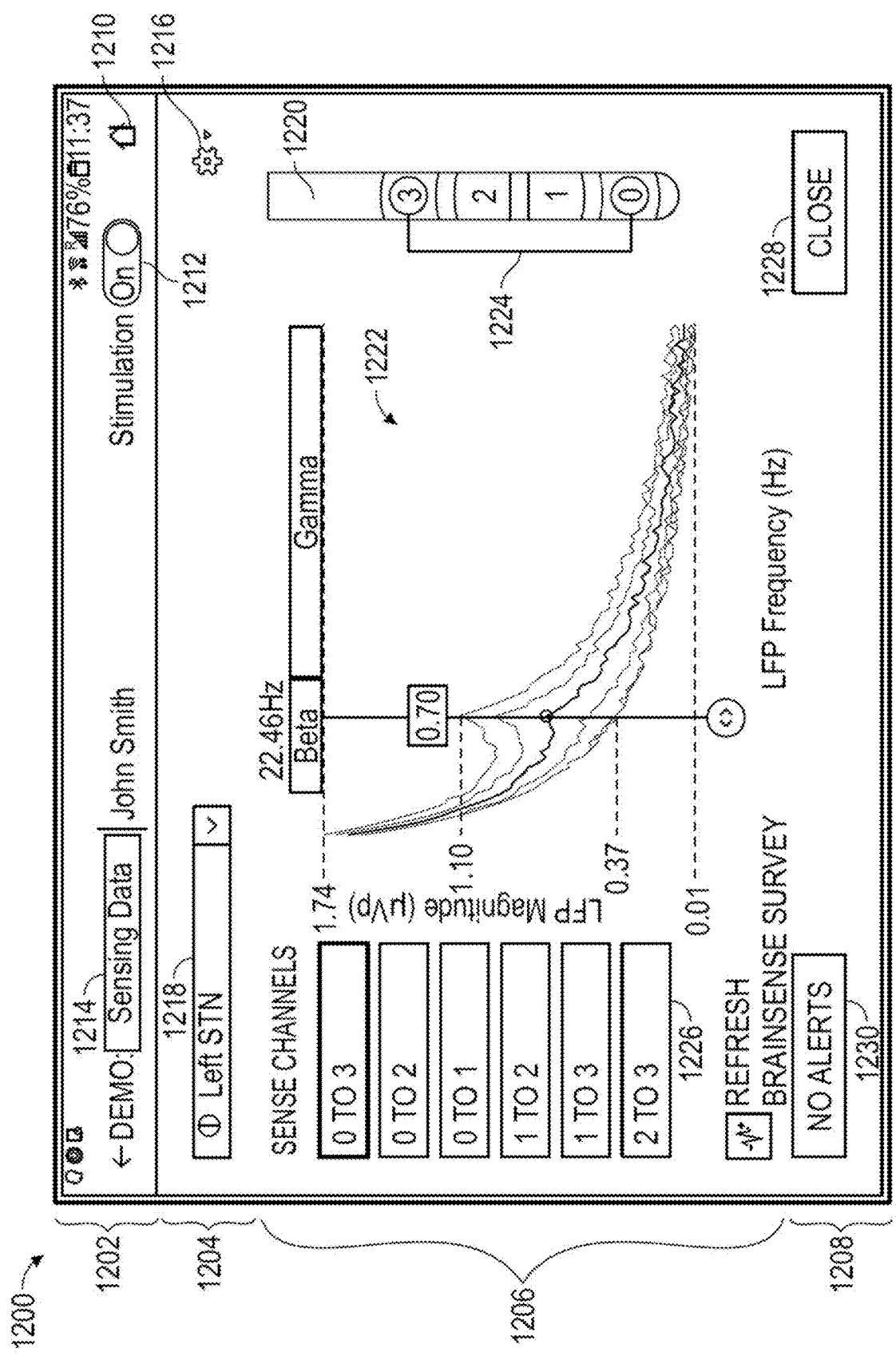
FIG. 12 illustrates an example user interface, in accordance with one or more techniques of this disclosure.

FIG. 12 illustrates an example user interface display, in accordance with one or more techniques of this disclosure. User interface 1200 may be presented on display 83 of FIG. 3. User Interface 1200 may be a representation of one portion, an axial electrode combination selection, of electrode selection module 87 (FIG. 3). User interface 1200 may allow a clinician to observe many aspects of a lead implantation procedure and IMD programming procedure. In some examples, user interface 1200 may also include other physical input hardware such as keyboards, mice, game pads and output hardware such as speakers, and printers. User interface 1200 may be a human-computer interface using interface layers to interact with one or more human sense, including: tactile, visual, auditory, olfactory, equilibria, and gustatory. User interface 1200 may provide a tactile and a visual user interface capable of displaying graphics.

User interface 1200 may be a standard, virtual and augmented graphical user interface. A standard display may use standard human interface devices like keyboards, mice, and computer monitors. A virtual display may block out the real world to create a virtual reality using a virtual reality interface. An augmented display may block out the real world and create an augmented reality interface.

User interface 1200 may be interactive or purely informational with a keyboard or other input device to interact with programmer 14 or other computing device, such as a mobile phone, laptop, tablet or desktop computer as discussed above. User interface 1200 may be a touch screen interactive display allowing the clinician to directly interact with programmer 14. In an example, user interface 1200 may allow clinicians to interact with programmer 14 through graphical icons and audio indicators such as primary notation.

The actions in user interface 1200 may be performed through direct manipulation of the graphical elements, such as directly touching the graphical elements on a screen to perform functions. In another example, user interface 1200 may provide text-based user interfaces typed command labels or text navigation command-line interfaces where the clinician may input commands to be typed on a computer keyboard. In another example, user interface 1200 may have a combination touch screen and text-based interface.

User interface 1200 may allow a clinician to observe lead location through coronal views, such as those shown in FIGS. 6 and 7. A clinician may observe sensed LFPs in an effort to locate target tissue 602 (FIGS. 6 and 7). In some examples, graphical representation of leads, such as leads 20, 400, 410, and 604, and electrodes, such as electrodes 24, 26, 404, 414, 500, 510, 520, 530, 606, 608, 610 and 612 may assist the physician in locating target tissue 602. Further, graphical representations may assist a clinician in determining an axial location of sensed LFPs as well as a direction of the sensed LFPs. By knowing an axial height and direction of the sensed LFPs a clinician may program effective therapy for a patient at a substantially reduced time.

As the number of electrodes on medical leads increase the time for bipolar review by a clinician when implanting medical leads increases. A bipolar review means the clinician is performing directional stimulation across all combinations of contacts and then assessing the effectiveness of the stimulation. This can make the implantation and programming procedure last up to three hours or even longer. User interface 1200 may provide LFP sensed spectral power data for a clinician and allow the clinician to determine a location for target tissue 602, thus substantially reducing the time for implantation and programming.

User interface 1200 may allow a clinician to determine, through graphical representation, relevant differences between electrode combinations by examining the spectral power between electrode combinations. User interface 1200 may assist a clinician to use LFPs spectral power to find electrode combinations closest to regions of the STN generating signals of interest, such as target tissue 602. With this information a clinician may be better informed to program direction stimulation using the electrode combinations selected by the clinician based upon displayed spectral power.

User interface 1200 may be comprised of a header 1202, a settings block 1204, a graphical display 1206, and a footer 1208. Header 1202 may be comprised of a home icon 1210, a stimulation status button 1212 and informational title 1214. Home icon 1210 may be a pictogram or ideogram displayed in order to help the clinician or user navigate. Home icon 1210 itself is a comprehensible symbol indicating touching home icon 1210 will take the clinician or user back to a "home", main or entry page for electrode selection module 87 (FIG. 3). Home icon 120 may serve as an electronic hyperlink or file shortcut to access electrode selection module 87. The clinician or user may activate home icon 1210 using a mouse, pointer, finger, or voice commands.

Also, within header 1202 may be stimulation status button 1212. Stimulation status button 1212 may be both informational and functional. Stimulation status button 1212 may provide information to a clinician or user as to whether system 10 is actively stimulating patient 12. Stimulation status button 1212 may brighten or even take on a bright hue, such as neon green, which may inform the clinician or user system 10 is actively stimulating. The clinician may interact with user interface 1200, by pushing on status button 1212 to stop stimulation of patient 12. Status button 1212 may imitate a real button and slide to the left, where the button would cover the words "On" and expose the words "Off". Further, the bright color would disappear, and a neutral unlit color may appear. This would indicate to the clinician and user system 10 is no longer stimulating patient 12. Further, status button 1212 is functional in that it may control the administration of stimulation.

Informational title 1214 may provide information to the clinician about patient 12 including a name, such as "John Smith". The information title may also include the name of the procedure, such as "Sensing Data." Further, information title 1214 may also include information such as what type of procedure is being performed, such as a demonstration or an active brain sensing of LFPs. An arrow shown in information title 1214 may allow the clinician or user to move back a step in the procedure.

Settings block 1204 may have a setting icon 1216 and a lead selection window 1218. Settings icon 1216 may be a drop-down window that allows the clinician or user to manipulate electrode selection module settings. Such settings may include selecting a background color for the display, inputting types of medical leads, inputting electrode configurations, modifying views or most any aspect to make the display of information more pleasing and useful to the clinician.

Selection window 1218 may allow the clinician or user to move between multiple implanted leads in patient 12. As shown in FIG. 12, a medical lead implanted in the left STN is being observed. The clinician may press on the down arrow in selection window 1218 to expose the other medical leads the clinician may want to observe in order to develop a stimulation therapy.

Graphical display 1206 may present graphical information to the clinician representative of an electrode combination selection. As may be shown in FIG. 12, a lead 1220 is shown on the right side of user interface 1200. Graphical display 1206, as shown, may be in the process of selecting an axial electrode combination. Each of the axially located electrodes are listed at 0, 1, 2, and 3. Further, user interface 1200 may display to the clinician the electrode pair that is being displayed in spectral power display 1222. As shown a line 1224 is connecting electrodes 0 and 3, that may represent the sensing of LFPs between the lowest most electrode and the upper most electrode on a lead. Spectral power display 1222, shows a representation of sensed LFPs through electrodes 0 and 3 and displays a peak at 22.46 Hz. The clinician may then cycle through the other combinations shown at electrode combination selection bar 1226. The clinician may cycle through each electrode combination using selection bar 1226 and pressing on the electrode combination they would like to examine. The clinician is looking for the electrode combination providing the largest peak on spectral power display 1222. This electrode combination may represent the electrodes which are closest to target tissue 602. Once the clinician has determined an electrode pair showing the greatest spectral power, the clinician may write down the electrode pair for later programming. In other examples, the clinician may press and hold on the electrode pair desired to have the electrode pair recorded in memory 82 (FIG. 3) for later use as the selected axial electrode pair. The clinician may shift to perform the same procedure on other leads through selection window 1218 where other leads may be chosen. The clinician may also press on the arrow in informational title 1214 to move to a procedure for identifying a circumferential electrode pair with a spectral power showing the best results for sensed LFPs.

Footer 1208 may have a way to exit electrode selection module 78 through graphical button 1228. Button 1228 may allow a clinician to end electrode selection module 78. Button 1228 may close the axial electrode selection portion of electrode selection module 78. Alert window 1230 may alert the clinician or user of any therapy system alerts, patient alerts or electrode selection module alerts. As shown in FIG. 12, there are no current alerts; however, should any alerts occur they may be displayed to the clinician in window 1230. Further, the alerts may be accompanied by varying types of colors depending on the urgency of the alert, such as green for a lower tier alert, yellow for a relatively important alert and red for a very important alert. Additionally, in some examples, an audible alarm may be present to gain the attention of the clinician. In another example, processing circuitry 80 or other device may generate an alert in response to determining that a significant change in level or directionality of spectral powers occurs since the last clinician visit. Such a change in the spectral powers from one or more electrode combinations may indicate potential lead damage, degradation of tissue, shift of the lead, and/or rotation of the lead. In another example, a significant change in the spectral power of electrode combinations in the strength or variation across electrodes over time (e.g., from the last clinic visit) may result from neural degeneration, inflammation, or other clinically relevant physiological change in the patient. Therefore, processor 80, another device, or the clinician, may identify changes in the patient due to changes in the level or directionality of determined spectral powers associated with one or more electrode combinations.

Figure 13:
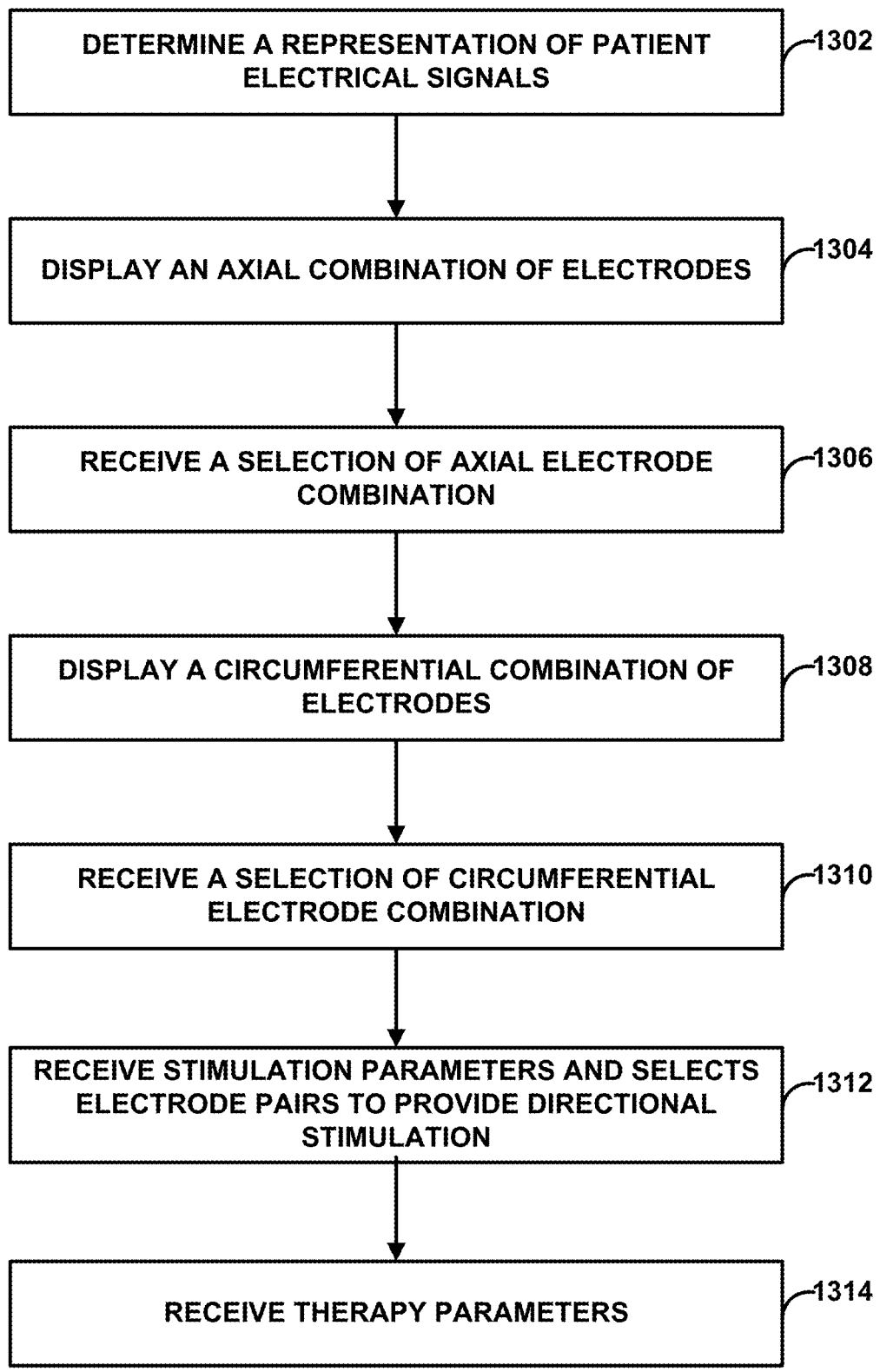
FIG. 13 illustrates a flow diagram of an example method for selecting electrode combinations for stimulation by an implanting clinician, in accordance with one or more techniques of this disclosure.

FIG. 13 is a flow diagram of an example technique for selecting an electrode combination to deliver electrical stimulation, in accordance with one or more techniques of this disclosure. For example, processing circuitry 80 of programmer 14, processor 60 or a processor of another computing device alone or in combination with processing circuitry 80, may perform any part of the techniques of FIG. 13.

As illustrated in FIG. 13, a device, such as processing circuitry 60 of IMD 16, may determine a representation of electrical signals for a particular patient (1302). As discussed above, a therapy system, such as therapy system 10, may be configured to sense bioelectrical brain signals of a patient. For instance, processing circuitry 60 may utilize one or more of electrodes 24, 26 of leads 20A and 20B, electrodes 404, 414 of leads 400 and 410, or electrodes 606, 608, 610 and 612 of lead 604 respectively, to measure a LFPs of the particular patient's brain across varying combinations of electrodes.

Display 83 may then display the representation of electrical signals for patient 12 (e.g., as shown in FIG. 12). Several axial combinations of electrodes sensing LFPs within patient 12 may be displayed (1304). In some examples, processing circuitry 80 may accept an input representing a selection of the axial electrode combination as discussed above in FIG. 12. A clinician may use display 83 in which to select a particular axial electrode combination of the plurality of axial electrode combinations. This selection may be stored in memory 82 (FIG. 3) to be used in the stimulation electrode combination. In some examples, each respective representation of electrical signals of the plurality of representations of electrical signals is associated with a respective electrode combination.

Display 83 may receive an input representative of a clinician's choice for an axial electrode pair closest to target tissue 602 (1306). A circumferential electrode combination for delivery of electrical stimulation therapy to the particular patient may be displayed (1308). The circumferential electrode combination may be from the same electrode level or different electrode level (where the electrode levels have circumferentially aligned electrodes or circumferential electrodes partially or fully offset). In some examples, the electrode combination may include electrodes from different electrode levels that also have different circumferential positions. For example, the two electrodes of the electrode combination may be from respective electrode levels that have partially or fully offset circumferential positions (e.g., as shown in leads 420 or 430). The axial electrode combination may be selected before or after the circumferential electrode combination is selected. The order of selection may be performed in any order.

Display 83 may receive an input representative of a clinician's choice for a circumferential electrode pair closest to target tissue 602 (1310). With an axial and circumferential electrode combination chosen, the clinician may then select a stimulation electrode combination based upon the axial electrode combination and the circumferential electrode combination. For example, the clinician may wish to have an electrode from the axial electrode combination and one from the circumferential electrode combination. Using, the example from FIG. 8 where axial electrode pair 608 and 610 were selected for an axial combination and the example from FIGS. 10A and 10B where circumferential electrode combination 606A and 606C were selected for a directional combination, a clinician may want to choose from these pairs to provide the best stimulation directional therapy to stimulate target tissue 602. Possible combinations for the anode and cathode may include:

a. 608C and 606C;
b. 608C and 606A;
c. 608A and 606C;
d. 608A and 606A;
e. 606A and 606C; and
f. 608A and 608C.

The clinician may choose the stimulation electrode combination from any one of these six combinations and input them into display 83 (1312). In an example of the present disclosure, programmer 14 may suggest an electrode combination to select. In another example, the programmer 14 may present identified axial and circumferential electrodes and the clinician may select the electrodes and polarity (if desired) to sense or for stimulation therapy. The clinician may also elect to keep the selected circumferential electrode pair that was located at an axial height in accordance with what the axial electrode combination sensing was showing. In another example, the clinician may perform an axial sensing between electrodes 606A, 606C, 608A and 608C to determine the electrode combination best suited to provide therapy to target tissue 602.

The clinician may now input therapy parameters of the stimulation therapy and store this therapy onboard memory 62 (FIG. 2) within therapy programs 74.

In another example, programmer 14 may use the following electrode combinations to acquire the spectral powers. Processing circuitry 80 may receive axial spectral power through the axial electrode combinations listed below:

a) 612-608
b) 612-606 c) 612-610
d) 608-606
e) 608-610
f) 606-610

Once the clinician or processing circuitry 80 has identified an axial electrode combination with the strongest spectral power, processing circuitry 80 may receive the circumferential spectral power through the electrode combinations listed below:

a) 608A-608B
b) 608B-608C
c) 608C-608A
d) 606A-606B
e) 606B-606C
f) 606C-606A

Once the clinician or processing circuitry 80 has identified a circumferential spectral power, processing circuitry 80 may determine an axial and circumferential spectral power. This third electrode combination may be utilized for stimulation therapy.

a. 608A-606A
b. 608B-606B
c. 608C-606C

This disclosure includes various examples, such as the following examples.

Figure 14:
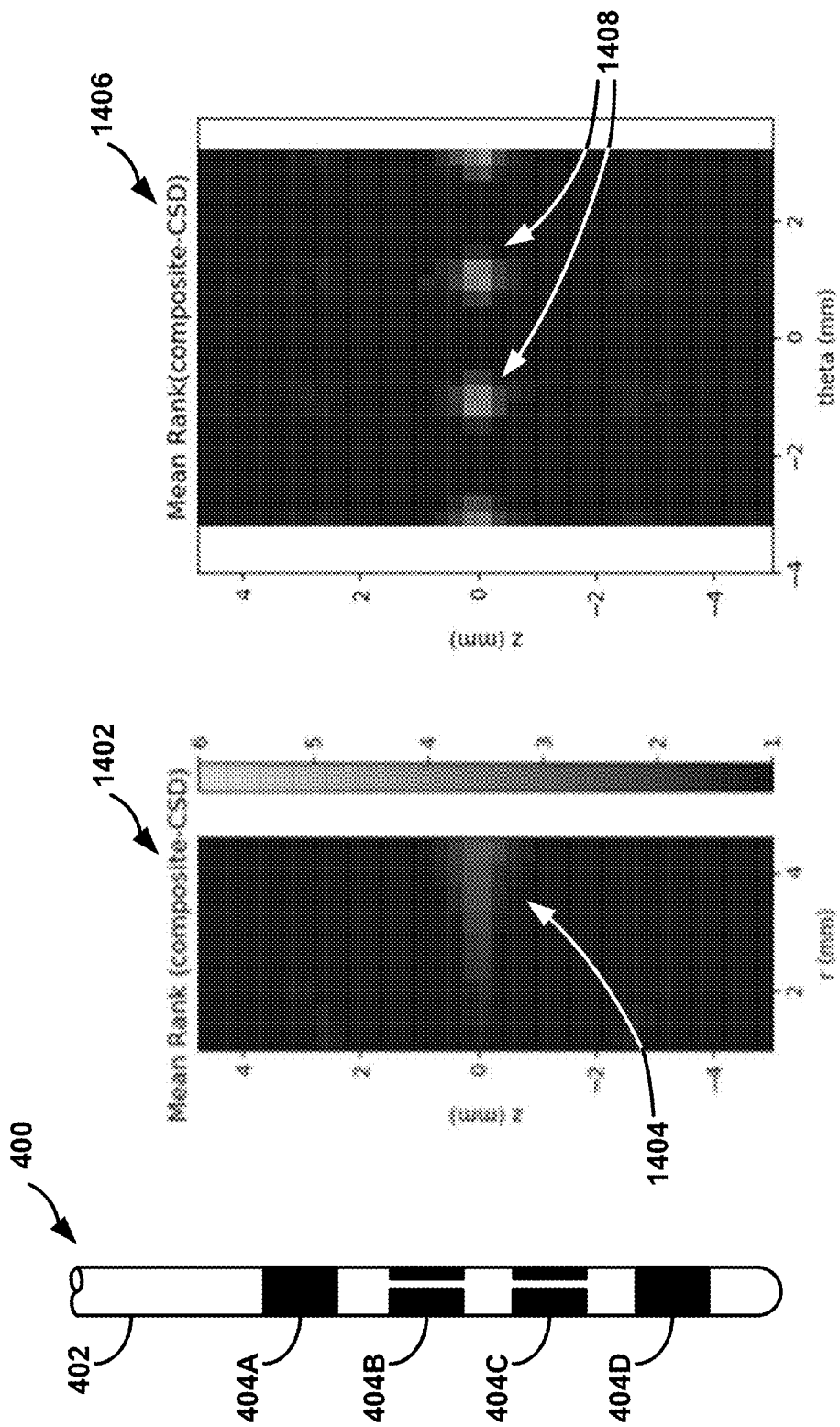
FIG. 14 is a conceptual diagram of example sensing power for different locations with respect to a lead.

FIG. 14 is a conceptual diagram of example sensing power for different locations with respect to a lead. As shown in FIG. 14, lead 400 includes circumferentially aligned electrodes in electrode levels 404B and 404C. Graph 1402 indicates the composite sensing magnitudes possible from electrode pairs of lead 400. Lighter values (approaching 6 on the vertical scale) indicate lower sensing magnitudes. Lower sensing magnitudes indicate "blind spots" in sensing and the electrode configurations of lead 400 are less able to detect signals (such as LFP oscillations) sensed at these locations. Graph 1402 indicates the composite sensing magnitudes at a radius "r" from the lead on the x-axis and at a vertical location "z" on the y-axis which corresponds to the locations of electrodes in lead 400 to the left. As shown in graph 1402, lead 400 is less able to detect signals originating between levels 404B and 404C as shown by blind spot 1404 that increase in size as the radial distance from lead 400 increases.

Graph 1406 indicates the composite sensing magnitudes at a circumferential position "theta" around the lead on the x-axis and at a vertical location "z" on the y-axis which corresponds to the locations of electrodes in lead 400 to the left. As shown in graph 1406, lead 400 is less able to detect signals originating between levels 404B and 404C and at the circumferential positions between respective electrodes of levels 404B and 404C, as shown by blind spots 1408. In other words, since the electrodes of electrode levels 404B and 404C are circumferentially aligned, the possible electrode pairs (e.g., electrode combinations that include only two electrodes), are less likely to detect signals originating from blind spots 1408. In some examples, larger electrode combinations can be used in an attempt to detect signals from these locations. However, the larger electrode combinations can reduce the sensitivity and detail of sensed data when compared to electrode pairs. Sensing from a lead that includes electrode levels with circumferentially offset electrodes can reduce the presence of blind spots and improve sensing and/or stimulation capability for some situations.

FIG. 15A is a conceptual diagram of an example lead 1510 with aligned circumferential electrodes and resulting sensing field 1522. As shown in the example of FIG. 15A, lead 1510 is presented in an unwrapped view to illustrate the respective locations of electrodes 1512 and 1518 and electrode levels 1514 and 1516, which would be similar to lead 400 of FIG. 4A. Each of electrode levels 1514 and 1516 include three electrodes, such as electrodes 1514A and 1516A, respectively.

If signal source 1520 is located between electrode levels 1514 and 1516 and circumferentially away from electrodes 1514A and 1516A, no electrode pair can appropriately detect the magnitude of the signals from signal source 1520. For example, as shown, sensing field 1522 that is capable of sensing signals between electrodes 1514A and 1516A may not adequately detect the signals from signal source 1520. Put another way, the magnitude of signals from signal source 1520 may be attenuated because electrodes 1514A and 1516A cannot detect all or most of the signal magnitude.

FIG. 15B is a conceptual diagram of an example lead 1530 with offset circumferential electrodes and resulting sensing field 1542. As shown in the example of FIG. 15B, lead 1530 is presented in an unwrapped view to illustrate the respective locations of electrodes 1532 and 1538 and electrode levels 1534 and 1536, which would be similar to lead 420 of FIG. 4C. Each of electrode levels 1534 and 1536 include three electrodes, such as electrodes 1534A and 1536A, respectively. The electrodes of electrode levels 1534 are circumferentially offset with the electrodes of electrode levels 1536.

If signal source 1520, just as shown in FIG. 15A, is located between electrode levels 1534 and 1536 and not directly between specific electrodes, multiple electrode pairs may be capable of appropriately detecting the magnitude of the signals from signal source 1520. This is in contrast to the capability of lead 1510. For example, as shown, sensing field 1542 is capable of sensing signals between electrodes 1534A and 1536A, on a diagonal with respect to the longitudinal axis of lead 1530, to adequately detect the signals from signal source 1520. Put another way, the magnitude of signals from signal source 1520 may be fully detected because electrodes 1514A and 1516A can detect all or most of the signal magnitude. In addition, for stimulating the tissue of signal source 1520, an electrode combination of electrodes 1534A and 1536A may require smaller amplitude to reach signal source 1520 than an electrode combination of electrodes 1514A and 1516A which are not as well positioned.

In this manner, the circumferentially offset electrodes of electrode levels 1534 and 1536 in lead 1530 may provide improved overall coverage (or comprehensive coverage) for sensing signals when compared to circumferentially aligned electrodes of lead 1510. More complete coverage can also provide improved LFP visualization of the tissue surrounding lead 1530 because the sensing electrode configurations can sense electrical signals over a larger volume of tissue. In addition, delivering stimulation from electrode combinations using circumferentially offset electrodes may improve directional flexibility in order to target desired anatomical locations. For example, electrode levels having circumferentially offset electrodes may enable a greater number of circumferential stimulation fields than would be possible with circumferentially aligned electrodes. Electrode combinations using circumferentially offset electrodes may also enable the system to generate more unique stimulation field shapes (e.g., volume of neural activation shapes) than otherwise possible from circumferentially aligned electrodes. Electrode combinations using circumferentially offset electrodes may also enable more efficient stimulation by using fewer electrodes than otherwise needed from circumferentially aligned electrodes requiring three or more electrodes to generate an electrical field to reach the desired target tissue.

Example 1A: A device comprising: sensing circuitry configured to sense electrical signals from a plurality of electrode combinations, each electrode of the plurality of electrode combinations carried by a medical lead, wherein the medical lead comprises electrodes at different axial positions along a length of the medical lead and at different circumferential positions around a perimeter of the medical lead; and processing circuitry configured to: identify, based on sensed electrical signals from a first subset of electrode combinations of the plurality of electrode combinations, a first electrode combination of the first subset of electrode combinations, wherein each electrode combination of the first subset of electrode combination comprises electrodes located at different axial positions along the length of the medical lead; identify, based on sensed electrical signals from a second subset of electrode combinations of the plurality of electrode combinations, a second electrode combination of the second subset of electrode combinations, wherein each electrode combination of the second subset of electrode combinations comprises electrodes located at a same axial position and different circumferential positions around the perimeter of the medical lead; determine, based on the first electrode combination and the second electrode combination, a third electrode combination; and control delivery of electrical stimulation via the third electrode combination.

Example 2A. The device of example 1A, wherein the sensed electrical signals comprise local field potentials (LFPs).

Example 3A. The device of example 2A, wherein the processing circuitry is configured to identify at least one of the first electrode combination or the second electrode combination based on a signal strength of sensed LFPs.

Example 4A. The device of example 3A, wherein the processing circuitry is configured to identify the at least one of the first electrode combination or the second electrode combination based on the signal strength of a Beta frequency band within the sensed LFPs.

Example 5A. The device of any of examples 1A through 4A, wherein at least one electrode combination of the first subset of electrode combinations comprises: a ring electrode extending circumferentially around the perimeter of the medial lead at a first axial position and set to a first polarity; and a plurality of electrodes extending circumferentially around the perimeter of the medical lead at a second axial position different than the first axial position, wherein the device is configured to combine the plurality of electrodes extending circumferentially around the perimeter of the medical lead at the second axial position to have a second polarity opposite the first polarity of the ring electrode, and wherein the sensing circuitry is configured to sense an axial electrical signal between the ring electrode and the combined plurality of electrodes extending circumferentially around the perimeter of the medical lead at the second axial position.

Example 6A. The device of any of examples 1A through 5A, wherein the processing circuitry is configured to determine one or more axial positions of electrodes of the third electrode combination based on an axial position of the identified first electrode combination.

Example 7A. The device of any of examples 1A through 6A, wherein at least one electrode combination of the second subset of electrode combinations comprises: a first electrode at a first circumferential position around the perimeter of the medical lead; and a second electrode at a second circumferential position around the perimeter of the medical lead, the second circumferential position being different than the first circumferential position.

Example 8A. The device of any of examples 1A through 7A, wherein the processing circuitry is configured to determine one or more circumferential positions of electrodes of the third electrode combination based on a circumferential position of the identified second electrode combination.

Example 9A. The device of any of examples 1A through 8A, wherein the processing circuitry is configured to identify the first electrode combination prior to identifying the second electrode combination.

Example 10A. The device of any of examples 1A through 9A, wherein the processing circuitry is configured to identify the second electrode combination prior to identifying the first electrode combination.

Example 11A. The device of any of examples 1A through 10A, wherein the third electrode combination comprises at least one of: one or more electrodes from the first electrode combination or one or more electrodes from the second electrode combination.

Example 12A. The device of any of examples 1A through 11A, wherein the processing circuitry is further configured to control telemetry circuitry to transmit information representative of the sensed electrical signals for presentation via a display of an external device.

Example 13A. The device of any of examples 1A through 12A, wherein the medical lead comprises a first set of electrodes at a first axial position and a second set of electrodes a second axial position different than the first axial position, wherein the first set of electrodes are circumferentially aligned with the second set of electrodes, and wherein one or more electrode combinations of the first subset of electrode combinations comprise one electrode of the first set of electrodes and at a first circumferential position and one electrode of the second set of electrodes and at the first circumferential position.

Example 14A. The device of any of examples 1A through 12A, wherein the medical lead comprises a first set of electrodes at a first axial position and a second set of electrodes a second axial position different than the first axial position, wherein the first set of electrodes are circumferentially offset from the second set of electrodes, and wherein one or more electrode combinations of the first subset of electrode combinations comprise one electrode of the first set of electrodes and at a first circumferential position and one electrode of the second set of electrodes and at a second circumferential position different from the first circumferential position.

Example 1B. A method comprising: sensing, by sensing circuitry, electrical signals from a plurality of electrode combinations, each electrode of the plurality of electrode combinations carried by a medical lead, wherein the medical lead comprises electrodes at different axial positions along a length of the medical lead and at different circumferential positions around a perimeter of the medical lead; identifying, by processing circuitry and based on sensed electrical signals from a first subset of electrode combinations of the plurality of electrode combinations, a first electrode combination of the first subset of electrode combinations, wherein each electrode combination of the first subset of electrode combination comprises electrodes located at different axial positions along the length of the medical lead; identifying, by the processing circuitry and based on sensed electrical signals from a second subset of electrode combinations of the plurality of electrode combinations, a second electrode combination of the second subset of electrode combinations, wherein each electrode combination of the second subset of electrode combinations comprises electrodes located at a same axial position and different circumferential positions around the perimeter of the medical lead; determining, by the processing circuitry and based on the first electrode combination and the second electrode combination, a third electrode combination; and controlling, by the processing circuitry, delivery of electrical stimulation via the third electrode combination.

Example 2B. The method of example 1B, wherein identifying the first electrode combination or the second electrode combination further comprises identifying, by the processing circuitry, a signal strength of sensed local field potentials (LFPs).

Example 3B. The method of example 2B, wherein the identifying the first electrode combination or the second electrode combination further comprises identifying a signal strength of a Beta frequency band within the sensed LFPs.

Example 4B. The method of any of examples 1B through 3B, wherein at least one electrode combination of the first subset of electrode combinations comprises a ring electrode extending circumferentially around the perimeter of the medial lead at a first axial position and set to a first polarity; and further comprising: combining a plurality of electrodes extending circumferentially around the perimeter of the medical lead at a second axial position different than the first axial position, wherein the plurality of electrodes extending circumferentially around the perimeter of the medical lead at the second axial position to have a second polarity opposite the first polarity of the ring electrode, and sensing, by the sensing circuitry, an axial electrical signal between the ring electrode and the combined plurality of electrodes extending circumferentially around the perimeter of the medical lead at the second axial position.

Example 5B. The method of any of examples 1B through 4B, further comprising determining, by the processing circuitry, one or more axial positions of electrodes of the third electrode combination based on an axial position of the identified first electrode combination.

Example 6B. The method of any of examples 1B through 5B, further comprising determining one or more circumferential positions of electrodes of the third electrode combination based on a circumferential position of the identified second electrode combination.

Example 7B. The method of any of examples 1B through 6B, wherein the identifying of the first electrode combination occurs prior to identifying the second electrode combination.

Example 8B. The method of any of examples 1B through 7B, wherein the medical lead comprises a first set of electrodes at a first axial position and a second set of electrodes a second axial position different than the first axial position, wherein the first set of electrodes are circumferentially aligned with the second set of electrodes, and wherein one or more electrode combinations of the first subset of electrode combinations comprise one electrode of the first set of electrodes and at a first circumferential position and one electrode of the second set of electrodes and at the first circumferential position.

Example 9B. The method of any of examples 1B through 7B, wherein the medical lead comprises a first set of electrodes at a first axial position and a second set of electrodes a second axial position different than the first axial position, wherein the first set of electrodes are circumferentially offset from the second set of electrodes, and wherein one or more electrode combinations of the first subset of electrode combinations comprise one electrode of the first set of electrodes and at a first circumferential position and one electrode of the second set of electrodes and at a second circumferential position different from the first circumferential position.

Example 1C. A computer-readable storage medium comprising instructions that, when executed, cause processing circuitry to: receive signal information indicative of first electrical signals sensed from a plurality of electrode combinations, each electrode of the plurality of electrode combinations carried by a medical lead, wherein the medical lead comprises electrodes at different axial positions along a length of the medical lead and at different circumferential positions around a perimeter of the medical lead; identify a first electrode combination of a first subset of electrode combinations of the plurality of electrode combinations, based on signal information from the first subset of electrode combinations of the plurality of electrode combinations, wherein each electrode combination of the first subset of electrode combination comprises electrodes located at different axial positions along the length of the medical lead; identify a second electrode combination of a second subset of electrode combinations of the plurality of electrode combinations based on signal information from a second subset of electrode combinations of the plurality of electrode combinations, wherein each electrode combination of the second subset of electrode combinations comprises electrodes located at a same axial position and different circumferential positions around the perimeter of the medical lead; and determine, a third electrode combination based on the first electrode combination and the second electrode combination; and control delivery of electrical stimulation via the third electrode combination.

As described herein, a system that employs directional brain sensing may reduce the time required to identify electrode combinations for sensing desired signals and/or delivering electrical stimulation therapy. In this manner, the systems described herein may improve clinician efficiency and treatment efficacy. This process is indeed advantageous considering the use of increasing number of electrodes on implantable leads (e.g., leads with electrodes disposed at different positions around the perimeter of the lead and at different positions along the length of the lead). Therefore, the techniques and systems described herein may enable the use of more electrodes that may improve targeting of desired tissue (e.g., specific regions of the brain associated with a disease, symptoms, or therapy) while reducing the time necessary for programming by the clinician.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored, as one or more instructions or code, on a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structures or any other structure suitable for implementation of the techniques described herein.

In addition, in some respects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques may be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples of the disclosure have been described. These and other examples are within the scope of the following claims.

What is claimed is:

1. A device comprising:
   sensing circuitry configured to sense electrical signals from a plurality of electrode combinations, each electrode of the plurality of electrode combinations carried by a medical lead, wherein the medical lead comprises electrodes at different axial positions along a length of the medical lead and at different circumferential positions around a perimeter of the medical lead; and
   processing circuitry configured to:
      identify, based on sensed electrical signals from a first subset of two or more electrode combinations of the plurality of electrode combinations, a first electrode combination of the first subset of electrode combinations, wherein each electrode combination of the first subset of electrode combination comprises electrodes located at different axial positions along the length of the medical lead;
      identify, based on sensed electrical signals from a second subset of two or more electrode combinations of the plurality of electrode combinations, a second electrode combination of the second subset of electrode combinations, wherein each electrode combination of the second subset of electrode combinations comprises electrodes located at a same axial position and different circumferential positions around the perimeter of the medical lead, and wherein the first electrode combination is different from the second electrode combination;
      determine, based on both the first electrode combination and the second electrode combination, a third electrode combination; and
      control delivery of electrical stimulation via the third electrode combination.

2. The device of claim 1, wherein the sensed electrical signals comprise local field potentials (LFPs).

3. The device of claim 2, wherein the processing circuitry is configured to identify at least one of the first electrode combination or the second electrode combination based on a signal strength of sensed LFPs.

4. The device of claim 3, wherein the processing circuitry is configured to identify the at least one of the first electrode combination or the second electrode combination based on the signal strength of a Beta frequency band within the sensed LFPs.

5. The device of claim 1, wherein at least one electrode combination of the first subset of electrode combinations comprises:
   a ring electrode extending circumferentially around the perimeter of the medial lead at a first axial position and set to a first polarity; and
   a plurality of electrodes extending circumferentially around the perimeter of the medical lead at a second axial position different than the first axial position, wherein the device is configured to combine the plurality of electrodes extending circumferentially around the perimeter of the medical lead at the second axial position to have a second polarity opposite the first polarity of the ring electrode, and wherein the sensing circuitry is configured to sense an axial electrical signal between the ring electrode and the combined plurality of electrodes extending circumferentially around the perimeter of the medical lead at the second axial position.

6. The device of claim 1, wherein the processing circuitry is configured to determine one or more axial positions of electrodes of the third electrode combination based on an axial position of the identified first electrode combination.

7. The device of claim 1, wherein at least one electrode combination of the second subset of electrode combinations comprises:
   a first electrode at a first circumferential position around the perimeter of the medical lead; and
   a second electrode at a second circumferential position around the perimeter of the medical lead, the second circumferential position being different than the first circumferential position.

8. The device of claim 1, wherein the processing circuitry is configured to determine one or more circumferential positions of electrodes of the third electrode combination based on a circumferential position of the identified second electrode combination.

9. The device of claim 1, wherein the processing circuitry is configured to identify the first electrode combination prior to identifying the second electrode combination.

10. The device of claim 1, wherein the processing circuitry is configured to identify the second electrode combination prior to identifying the first electrode combination.

11. The device of claim 1, wherein the third electrode combination comprises one or more electrodes from the first electrode combination and one or more electrodes from the second electrode combination, and wherein the third electrode combination is different from both the first electrode combination and the second electrode combination.

12. The device of claim 1, wherein the processing circuitry is further configured to control telemetry circuitry to transmit information representative of the sensed electrical signals for presentation via a display of an external device.

13. The device of claim 1, wherein the medical lead comprises a first set of electrodes at a first axial position and a second set of electrodes a second axial position different than the first axial position, wherein the first set of electrodes are circumferentially aligned with the second set of electrodes, and wherein one or more electrode combinations of the first subset of electrode combinations comprise one electrode of the first set of electrodes and at a first circumferential position and one electrode of the second set of electrodes and at the first circumferential position.

14. The device of claim 1, wherein the medical lead comprises a first set of electrodes at a first axial position and a second set of electrodes a second axial position different than the first axial position, wherein the first set of electrodes are circumferentially offset from the second set of electrodes such that all circumferential positions of the first set of electrodes are different than circumferential positions of the second set of electrodes, and wherein one or more electrode combinations of the first subset of electrode combinations comprise one electrode of the first set of electrodes and at a first circumferential position and one electrode of the second set of electrodes and at a second circumferential position different from the first circumferential position.

15. A method comprising:
sensing, by sensing circuitry, electrical signals from a plurality of electrode combinations, each electrode of the plurality of electrode combinations carried by a medical lead, wherein the medical lead comprises electrodes at different axial positions along a length of the medical lead and at different circumferential positions around a perimeter of the medical lead;
identifying, by processing circuitry and based on sensed electrical signals from a first subset of two or more electrode combinations of the plurality of electrode combinations, a first electrode combination of the first subset of electrode combinations, wherein each electrode combination of the first subset of electrode combination comprises electrodes located at different axial positions along the length of the medical lead;
identifying, by the processing circuitry and based on sensed electrical signals from a second subset of two or more electrode combinations of the plurality of electrode combinations, a second electrode combination of the second subset of electrode combinations, wherein each electrode combination of the second subset of electrode combinations comprises electrodes located at a same axial position and different circumferential positions around the perimeter of the medical lead, and wherein the first electrode combination is different from the second electrode combination;
determining, by the processing circuitry and based on both the first electrode combination and the second electrode combination, a third electrode combination; and
controlling, by the processing circuitry, delivery of electrical stimulation via the third electrode combination.

16. The method of claim 15, wherein identifying the first electrode combination or the second electrode combination further comprises identifying, by the processing circuitry, a signal strength of sensed local field potentials (LFPs).

17. The method of claim 16, wherein the identifying the first electrode combination or the second electrode combination further comprises identifying a signal strength of a Beta frequency band within the sensed LFPs.

18. The method of claim 15, wherein at least one electrode combination of the first subset of electrode combinations comprises a ring electrode extending circumferentially around the perimeter of the medial lead at a first axial position and set to a first polarity; and further comprising:
combining a plurality of electrodes extending circumferentially around the perimeter of the medical lead at a second axial position different than the first axial position, wherein the plurality of electrodes extending circumferentially around the perimeter of the medical lead at the second axial position to have a second polarity opposite the first polarity of the ring electrode, and
sensing, by the sensing circuitry, an axial electrical signal between the ring electrode and the combined plurality of electrodes extending circumferentially around the perimeter of the medical lead at the second axial position.

19. The method of claim 15, further comprising determining, by the processing circuitry, one or more axial positions of electrodes of the third electrode combination based on an axial position of the identified first electrode combination.

20. The method of claim 15, further comprising determining one or more circumferential positions of electrodes of the third electrode combination based on a circumferential position of the identified second electrode combination.

21. The method of claim 15, wherein the identifying of the first electrode combination occurs prior to identifying the second electrode combination.

22. The method of claim 15, wherein the medical lead comprises a first set of electrodes at a first axial position and a second set of electrodes a second axial position different than the first axial position, wherein the first set of electrodes are circumferentially aligned with the second set of electrodes, and wherein one or more electrode combinations of the first subset of electrode combinations comprise one electrode of the first set of electrodes and at a first circumferential position and one electrode of the second set of electrodes and at the first circumferential position.

23. The method of claim 15, wherein the medical lead comprises a first set of electrodes at a first axial position and a second set of electrodes a second axial position different than the first axial position, wherein the first set of electrodes are circumferentially offset from the second set of electrodes such that all circumferential positions of the first set of electrodes are different than circumferential positions of the second set of electrodes, and wherein one or more electrode combinations of the first subset of electrode combinations comprise one electrode of the first set of electrodes and at a first circumferential position and one electrode of the second set of electrodes and at a second circumferential position different from the first circumferential position.

24. A non-transitory computer-readable storage medium comprising instructions that, when executed, cause processing circuitry to:
receive signal information indicative of first electrical signals sensed from a plurality of electrode combinations, each electrode of the plurality of electrode combinations carried by a medical lead, wherein the medical lead comprises electrodes at different axial positions along a length of the medical lead and at different circumferential positions around a perimeter of the medical lead;
identify a first electrode combination of a first subset of two or more electrode combinations of the plurality of electrode combinations, based on signal information from the first subset of electrode combinations of the plurality of electrode combinations, wherein each electrode combination of the first subset of electrode combination comprises electrodes located at different axial positions along the length of the medical lead;
identify a second electrode combination of a second subset of two or more electrode combinations of the plurality of electrode combinations based on signal information from a second subset of electrode combinations of the plurality of electrode combinations, wherein each electrode combination of the second subset of electrode combinations comprises electrodes located at a same axial position and different circumferential positions around the perimeter of the medical lead, and wherein the first electrode combination is different from the second electrode combination; and determine, a third electrode combination based on both the first electrode combination and the second electrode combination; and control delivery of electrical stimulation via the third electrode combination.

* * * * *